(12) United States Patent
Riley et al.

(10) Patent No.: US 8,281,433 B2
(45) Date of Patent: Oct. 9, 2012

(54) APPARATUSES FOR SUPPORTING AND MONITORING A PERSON

(75) Inventors: Carl William Riley, Milan, IN (US); Timothy J. Receveur, Guilford, IN (US); David L. Ribble, Indianapolis, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 413 days.

(21) Appl. No.: 12/581,951

(22) Filed: Oct. 20, 2009

(65) Prior Publication Data

US 2010/0101022 A1 Apr. 29, 2010

Related U.S. Application Data

(60) Provisional application No. 61/108,485, filed on Oct. 24, 2008, provisional application No. 61/112,002, filed on Nov. 6, 2008.

(51) Int. Cl.
*A47B 71/00* (2006.01)

(52) U.S. Cl. ............. 5/600; 5/613; 5/617; 5/940; 5/616; 128/845

(58) Field of Classification Search .............. 5/600, 613, 5/617, 940, 616; 128/845
See application file for complete search history.

(56) References Cited

U.S. PATENT DOCUMENTS

| | | |
|---|---|---|
| 2,194,809 A | 3/1940 | Powell, Jr. |
| 3,325,799 A | 6/1967 | Farris |
| 3,631,438 A | 12/1971 | Lewin |
| 3,644,950 A | 2/1972 | Lindsay, Jr. |
| 3,727,606 A | 4/1973 | Sielaff |
| 3,836,900 A | 9/1974 | Mansfield |
| 3,996,928 A | 12/1976 | Marx |
| 4,146,885 A | 3/1979 | Lawson, Jr. |
| 4,195,287 A | 3/1980 | McCoy et al. |
| 4,245,651 A | 1/1981 | Frost |
| 4,422,458 A | 12/1983 | Kravath |
| 4,481,686 A | 11/1984 | Lacoste |
| 4,483,029 A | 11/1984 | Paul |
| 4,485,505 A | 12/1984 | Paul |
| 4,525,885 A | 7/1985 | Hunt et al. |
| 4,559,656 A | 12/1985 | Foster |
| 4,564,965 A | 1/1986 | Goodwin |
| 4,595,023 A | 6/1986 | Bonnet |
| 4,602,643 A | 7/1986 | Dietz |
| 4,637,083 A | 1/1987 | Goodwin |
| 4,657,026 A | 4/1987 | Tagg |
| 4,677,857 A | 7/1987 | Feldmann |
| 4,681,098 A | 7/1987 | Lee |
| 4,694,520 A | 9/1987 | Paul et al. |

(Continued)

FOREIGN PATENT DOCUMENTS

JP 06315424 A2 11/1994

OTHER PUBLICATIONS

International Search Report/Written Opinion for PCT/US2009/061229 completed Feb. 9, 2010.

*Primary Examiner* — Robert G Santos
*Assistant Examiner* — David E. Sosnowski
(74) *Attorney, Agent, or Firm* — Barnes & Thornburg LLP

(57) ABSTRACT

Embodiments disclosed herein related to person support apparatuses and systems, and in particular, to such apparatuses and systems that incorporate or are used with vital signs monitoring devices.

15 Claims, 15 Drawing Sheets

U.S. PATENT DOCUMENTS

| | | |
|---|---|---|
| 4,757,825 A | 7/1988 | Diamond |
| 4,799,276 A | 1/1989 | Kadish |
| 4,838,309 A | 6/1989 | Goodwin |
| 4,889,131 A | 12/1989 | Salem et al. |
| 4,934,468 A | 6/1990 | Koerber, Sr. et al. |
| 4,935,968 A | 6/1990 | Hunt et al. |
| 4,942,635 A | 7/1990 | Hargest et al. |
| 4,949,412 A | 8/1990 | Goode |
| 4,949,414 A | 8/1990 | Thomas et al. |
| 4,971,065 A | 11/1990 | Pearce |
| 5,010,772 A | 4/1991 | Bourland et al. |
| 5,052,067 A | 10/1991 | Thomas et al. |
| 5,057,819 A | 10/1991 | Valenti |
| 5,060,174 A | 10/1991 | Gross |
| 5,101,828 A | 4/1992 | Welkowitz et al. |
| 5,117,518 A | 6/1992 | Schild |
| 5,170,364 A | 12/1992 | Gross et al. |
| 5,182,826 A | 2/1993 | Thomas et al. |
| 5,184,112 A | 2/1993 | Gusakov |
| 5,283,735 A | 2/1994 | Gross et al. |
| 5,539,942 A | 7/1996 | Melou |
| 5,664,270 A | 9/1997 | Bell et al. |
| 5,794,288 A | 8/1998 | Soltani et al. |
| 5,815,864 A | 10/1998 | Sloop |
| 5,817,146 A | 10/1998 | Augustine |
| 5,829,081 A | 11/1998 | Pearce |
| 5,873,137 A | 2/1999 | Yavets-Chen |
| 5,934,280 A | 8/1999 | Viard et al. |
| 5,964,720 A | 10/1999 | Pelz |
| 5,970,789 A | 10/1999 | Meyer et al. |
| 6,009,580 A | 1/2000 | Caminade et al. |
| 6,011,477 A | 1/2000 | Teodorescu et al. |
| 6,034,526 A | 3/2000 | Montant et al. |
| 6,067,019 A | 5/2000 | Scott |
| 6,079,068 A | 6/2000 | Viard |
| 6,094,762 A | 8/2000 | Viard et al. |
| 6,208,250 B1 | 3/2001 | Dixon et al. |
| 6,212,718 B1 | 4/2001 | Stolpmann et al. |
| 6,493,568 B1 | 12/2002 | Bell et al. |
| 6,721,980 B1 | 4/2004 | Price et al. |
| 6,739,006 B2 | 5/2004 | Borders et al. |
| 6,984,207 B1 | 1/2006 | Sullivan et al. |
| 7,077,810 B2 | 7/2006 | Lange et al. |
| 7,127,948 B2 | 10/2006 | Tavares et al. |
| 7,183,930 B2 | 2/2007 | Basir et al. |
| 7,242,306 B2 | 7/2007 | Wildman et al. |
| 7,245,956 B2 | 7/2007 | Matthews et al. |
| 7,248,933 B2 | 7/2007 | Wildman |
| 7,253,366 B2 | 8/2007 | Bhai |
| 7,296,312 B2 | 11/2007 | Menkedick et al. |
| 7,304,580 B2 | 12/2007 | Sullivan et al. |
| 7,306,564 B2 | 12/2007 | Nakatani et al. |
| 7,314,451 B2 | 1/2008 | Halperin et al. |
| 7,315,535 B2 | 1/2008 | Schuman |
| 7,319,386 B2 | 1/2008 | Collilns, Jr. et al. |
| 7,330,127 B2 | 2/2008 | Price et al. |
| 7,515,059 B2 | 4/2009 | Price et al. |
| 7,629,890 B2 | 12/2009 | Sullivan et al. |
| 2001/0004778 A1 | 6/2001 | Heimbrock et al. |
| 2004/0111045 A1 | 6/2004 | Sullivan et al. |
| 2005/0027416 A1 | 2/2005 | Basir et al. |
| 2005/0168341 A1 | 8/2005 | Reeder et al. |
| 2005/0190062 A1 | 9/2005 | Sullivan et al. |
| 2005/0190068 A1 | 9/2005 | Gentry et al. |
| 2006/0101581 A1 | 5/2006 | Blanchard et al. |
| 2006/0179952 A1 | 8/2006 | Tavares et al. |
| 2007/0118054 A1 | 5/2007 | Pinhas et al. |
| 2008/0060138 A1 | 3/2008 | Price et al. |
| 2008/0114260 A1 | 5/2008 | Lange et al. |
| 2008/0269625 A1 | 10/2008 | Halperin et al. |
| 2008/0275349 A1 | 11/2008 | Halperin et al. |

APPARATUSES FOR SUPPORTING AND MONITORING A PERSON

This application claims the benefit, under 35 U.S.C. §119 (e), of U.S. Provisional Application No. 61/108,485 which was filed Oct. 24, 2008 and U.S. Provisional Application No. 61/112,002 which was filed Nov. 6, 2008, the disclosures of each of which are hereby incorporated by reference herein.

BACKGROUND

The present disclosure relates to person support apparatuses such as hospital beds that are used in healthcare facilities such as hospitals and nursing homes. In particular, the present disclosure relates to patient support apparatuses that incorporate or are used with physiological monitoring devices.

Person support apparatuses can comprise beds, chairs, stretchers, seats, mattresses, therapy surfaces, furniture, and the like, or other apparatuses that support a person. Hospital beds and stretchers, hospital mattresses, and wheelchairs are examples of such apparatuses that support persons in healthcare facilities. Consumer beds, chairs, and furniture are also examples of such person support apparatuses, as are seats for vehicles, businesses, and venues.

Vital signs monitors can monitor one or more physiological parameters of a person, such as body temperature, pulse rate, heart rate, blood pressure, and respiratory rate, as well as other body signs, such as end-tidal CO2, SpO2 (saturation of oxygen in arterial blood flow), and other indicators of the person's physiological state.

There is a persistent need for further contributions and improvements in these areas of technology.

SUMMARY

The present invention comprises one or more of the features recited in the appended claims and/or the following features which, alone or in any combination, may comprise patentable subject matter:

An apparatus for supporting and contactless monitoring of a person may comprise a bedframe and a mattress support deck coupled to the bed frame. The mattress support deck may include a head deck section that is movable between a raised position and a lowered position and that is configured to support the person's upper body. The apparatus may further comprise a sensing device fixed to the head deck section and configured to provide a monitoring signal indicative of at least one physiological sign of the person. A processor may be coupled to the bedframe and may be configured to receive the monitoring signal.

The sensing device may be embedded in the head deck section. In some embodiments, the head deck section may be molded around the sensing device so as to completely encase the sensing device. The sensing device may comprise a piezoelectric element that is placed under stress by stress that is induced in the head deck section during a molding process. Alternatively or additionally, the sensing device may comprise a housing and a piezoelectric diaphragm member in a stressed state within the housing.

A second sensing device may be fixed to the bedframe and may be configured to sense at least one physiological sign of the person. The mattress support deck may comprises a seat deck section adjacent the head deck section and the apparatus may further comprise a second sensing device fixed to the seat deck section and configured to sense at least one physiological sign of the person.

In some embodiments, the head deck section may have a substantially non-planar in shape. For example, the head deck section may have a generally parabolic shape. Thus, the head deck section may be curved along its length and along its width.

The apparatus may further comprise a waveguide coupled to the sensing device and configured to transmit energy to the sensing device. The waveguide may comprise at least one of the following: a beam member, a wire member, and a strip member. The sensing device may comprise an array of spaced apart piezoelectric sensor devices.

The head deck section may have a first side edge and a second side edge and the sensing device may be located about midway between the first and second side edges. Therefore, the sensing device may be fixed to the head deck section at a central region of the head deck section.

Also according to this disclosure, a patient support surface may comprise a cover defining an interior region, a support layer situated in the interior region, a first sensing device situated in the interior region above the support layer, and a second sensing device situated in the interior region beneath the support layer. The first and second sensors may be configured to provide at least one monitoring signal indicative of at least one physiological sign of a patient atop the patient support surface.

The support layer may comprise at least one air bladder. The at least one air bladder may, in turn, comprise a turn bladder that is inflated to turn a patient toward one of the patient's sides. According to this disclosure, at least one air bladder in the interior region may overlie the support layer and the first and second sensing devices. A processor assembly may be located inside the interior region and may be electrically coupled to the first and second sensing devices.

In one embodiment, an apparatus for supporting and contactless monitoring of a person is provided. The apparatus comprises a person support apparatus, a sensing device coupled to the person support apparatus and a processor coupled to the person support apparatus. The sensing device is configured to provide a monitoring signal indicative of at least one physiological sign of a person supported on the person support apparatus without contacting the person. The processor is configured to receive the monitoring signal and to determine a physiological sign of the person based upon at least the monitoring signal. In one embodiment, the sensing device is coupled by integral formation within a member of the person support apparatus, such as a deck member or frame member for example. In one embodiment, the processor is housed in an electronics housing attached to the person support apparatus. In one embodiment, the processor detects heart rate and the processor determines the onset of an adverse heart episode based upon at least the heart rate.

In another embodiment, an apparatus is provided for supporting and contactless monitoring of a person. The apparatus comprises a person support apparatus having a deck section configured such that at least a portion of a person may be placed directly or indirectly on the deck section. The apparatus further comprises a sensing device coupled to the deck section of the person support apparatus. The sensing device is configured to provide a monitoring signal indicative of at least one physiological sign of a person supported on the person support apparatus without contacting the person.

According to another embodiment, the apparatus comprises a person support apparatus having a torso deck section (sometimes referred to as a head deck section or just a head section) configured such that at least a portion of a person's torso may be placed directly or indirectly on the torso deck section. The person support apparatus further includes a seat deck section configured such that at least a portion of a person's seat area may be placed directly or indirectly on the seat deck section. The apparatus further comprises a first sensing device coupled to the torso deck section of the person support apparatus. The first sensing device is configured to provide a monitoring signal indicative of at least one physiological sign of a person supported on the person support apparatus without contacting the person. A second sensing device is coupled to the seat deck section of the person support apparatus and configured to provide a monitoring signal indicative of at least one physiological sign of a person supported on the person support apparatus without contacting the person. The first and second sensing devices can be embedded within their respective deck sections, if desired.

The apparatus may further comprise, in some embodiments, a processor coupled to the person support apparatus and configured to receive the monitoring signal and determine the onset of a physiological episode based upon the monitoring signal. In some embodiments, the episode comprises at least one of a heart attack, congestive heart failure, endocarditis, myocarditis, coronary artery disease, cardiomyopathy, asthma, cystic fibrosis (CF), and chronic obstructive pulmonary disease (COPD).

In yet another embodiment, the apparatus comprises a deck section with a substantially non-planar shape. The apparatus of this embodiment further comprises a sensing device coupled to the deck section of the person support apparatus. The sensing device is configured to provide a monitoring signal indicative of at least one physiological sign of a person supported on the person support apparatus without contacting the person. The sensing device is coupled at a location on the deck section such that forces from a person supported by the deck section are transmitted through the portion of the deck section having the non-planar shape. The portion of the deck section has a generally parabolic shape in one embodiment.

In yet another embodiment, at least one beam member supports the deck section. A sensing device is coupled to the deck section of the person support apparatus and configured to provide a monitoring signal indicative of at least one physiological sign of a person supported on the person support apparatus without contacting the person. The sensing device is coupled at a location on the deck section such that forces from a person supported by the deck section are transmitted through the deck section and arrive at the sensing device without being transmitted to the beam member. In one embodiment, a processor is coupled to the person support apparatus and configured to receive the monitoring signal and determine the onset of a physiological episode based upon the monitoring signal. The episode may comprise at least one of a heart attack, congestive heart failure, endocarditis, myocarditis, coronary artery disease, cardiomyopathy, asthma, cystic fibrosis (CF), and chronic obstructive pulmonary disease (COPD).

According to some embodiments contemplated herein, a sensing device is coupled to the deck section of the person support apparatus and is configured to provide a monitoring signal indicative of at least one physiological sign of a person supported on the person support apparatus without contacting the person. The sensing device is coupled at a location on the deck section that is closer to the middle of the deck section than is any portion of the beam member. A processor may be coupled to the person support apparatus and configured to receive the monitoring signal and determine the onset of a physiological episode based upon the monitoring signal.

According to another embodiment, a waveguide is coupled to the deck section and is configured to transmit energy, such as mechanical movement or sound, from one part of the person support apparatus to another part of the person support apparatus. A sensing device is coupled to the waveguide and is configured to provide a monitoring signal indicative of at least one physiological sign of a person supported on the person support apparatus without contacting the person. For example, the sensing device may be mechanically coupled with the waveguide in some embodiments. The waveguide may comprise a beam or wire or strip in some embodiments.

According to a further embodiment, an apparatus is provided for supporting and contactless monitoring of a person and includes a first cushioning and/or support layer and a second cushioning and/or support layer. A sensing device is located adjacent at least one of the first and second layers and configured to provide a monitoring signal indicative of at least one physiological sign of a person supported on the person support apparatus without contacting the person. The cushioning layers may comprise foam and/or air bladders, and a cover may enclose the layers, in some embodiments. The cover may include an antimicrobial material in some embodiments, if desired.

In yet another embodiment, an apparatus for supporting and contactless monitoring of a person comprises at least one air bladder and a sensing device that is located above or below the air bladder and that is configured to provide a monitoring signal indicative of at least one physiological sign of a person supported on the person support apparatus without contacting the person. The apparatus may further comprise foam. In some embodiments, a processor is located within or adjacent the person support apparatus and configured to receive the monitoring signal and determine the onset of a physiological episode based upon the monitoring signal. The episode can comprise at least one of a heart episode, skin condition, and a breathing episode.

In a further embodiment, at least one sensing device is located above or below the air bladder of a patient support surface and is configured to provide a monitoring signal indicative of at least one physiological sign of a person supported on the person support apparatus without contacting the person. A plurality of sensing devices may be provided above and/or below the air bladder in other embodiments.

According to this disclosure, therefore, the apparatus may comprise a mattress comprising at least one air bladder and a cover enclosing the air bladder. A sensing device may be located within the cover and configured to provide a monitoring signal indicative of at least one physiological sign of a person supported on the mattress. In some embodiments, a processor is located within or adjacent the mattress and configured to receive the monitoring signal and determine the onset of a physiological episode based upon the monitoring signal. The episode may comprise at least one of a heart episode, skin condition, and a breathing episode.

In another embodiment, an apparatus is provided for supporting and contactless monitoring of a person. The apparatus comprises a mattress having at least one cushioning layer, and a cover enclosing the cushioning layer. A sensing device is located within the cover and configured to provide a monitoring signal indicative of at least one physiological sign of a person supported on the mattress. A processor can be located within or adjacent the mattress and configured to receive the monitoring signal and determine the onset of a physiological episode based upon the monitoring signal, in some embodiments.

In a further embodiment, an apparatus is provided for supporting and contactless monitoring of a person. The apparatus includes a mattress comprising a first cushioning layer and a second cushioning layer. A sensing device is located at least partially between the layers to provide a monitoring signal indicative of at least one physiological parameter of a person supported on the mattress without contacting the person. The layers may comprise foam and/or air bladders. In some embodiments, a processor is located within or adjacent the mattress and configured to receive the monitoring signal and determine the onset of a physiological episode based upon the monitoring signal. In some embodiments, the layers may comprise foam of differing durometers. A rigid support can be located adjacent at least one of the first and second layers, and the sensing device located between the rigid support and at least one of the first and second layers.

In another embodiment, an apparatus is provided for supporting and contactless monitoring of a person. The apparatus of this embodiment comprises a person support apparatus having a support surface configured to support a person in at least one of a seated and supine position. An opening is located beneath at least a portion of the support surface. A sensing device is located at least partially within the opening and configured to provide a monitoring signal indicative of at least one physiological sign of a person supported on the mattress. The sensing device is coupled with a cassette in some embodiments. The cassette can be slidably removable within the opening and mate with a connector adjacent the opening. In some embodiments, the sensing device is held between two rigid sheets. In some embodiments, the sensing device is coupled to the person support apparatus via a connector which connects to the sensing device via an interference fit or a snap in connection, and the sensing device includes an electrical connector that couples with a connector in the person support apparatus.

According to another embodiment, an apparatus is provided for supporting and contactless monitoring of a person. The apparatus of this embodiment includes a person support apparatus having a surface configured for supporting a person in at least one of a sitting and supine position, and a support layer beneath the surface. A sensing device is located between the surface and the support layer and configured to provide a monitoring signal indicative of at least one physiological sign of a person supported on the person support apparatus without contacting the person. In some embodiments, at least one weight sensor, an output device, and a processor are also provided. The weight sensor is configured to obtain the person weight at multiple locations along the person support apparatus. The output device is configured to provide an output signal indicative of the physiological sign based upon the monitoring signal. The processor is configured to receive the person's weight from the person sensor and to directly or indirectly adjust at least one of the sensing device, the monitoring signal, and the output signal based upon the person weights. In some embodiments, the weight sensor comprises an inductance sensor or a load cell, and the sensing device comprises a piezoelectric sensor.

In another embodiment, an apparatus is provided for supporting and contactless monitoring of a person, comprising a person support apparatus, a sensing device and a housing. The person support apparatus has a support surface for supporting a person in at least one of a sitting and a supine position. The sensing device is configured to provide a monitoring signal indicative of at least one physiological sign of a person supported on the person support apparatus without contacting the person. The housing is coupled with the person support apparatus and includes a processor configured to receive the monitoring signal from the sensing device. In some embodiments, a power supply is provided and configured for providing power to at least one component of the person support apparatus, as well as to the processor. In some embodiments, a user interface is provided and configured to control at least one function of the person support apparatus by a user. The user interface is further configured for displaying data under control of the processor and/or setting the operation of the processor via an input to the user interface. In some embodiments, the processor is configured to display data representing the physiological sign, indicate an alarm based upon the monitoring signal, and/or determine the onset of an episode based upon the monitoring signal. In some embodiments, the person support apparatus comprises a bed, mattress or chair with a movable component, and the apparatus further comprises a user interface configured to control the movable component via input from a user, to provide input to the processor and/or sensing device, and/or to display output originating from the processor and/or sensing device.

According to a further embodiment, an apparatus is provided for supporting and contactless monitoring of a person comprising a person support apparatus and a moving component. The person support apparatus has a support surface configured for supporting a person in at least one of a sitting and supine position. The moving component is configured to provide a therapy to the person when supported on the support surface. A sensing device is coupled with the person support apparatus and configured to provide a monitoring signal indicative of at least one physiological sign of a person supported on the person support apparatus without contacting the person while the moving component is providing therapy. In some embodiments, the person support apparatus comprises a mattress and the moving component comprises an air bladder, and the therapy comprises alternating pressure therapy, continuous lateral rotation therapy, and/or low air loss therapy. In some embodiments, the apparatus can further comprise a processor configured to process the monitoring signal and determine the onset of an episode based upon the monitoring signal. The episode can comprise at least one of a heart episode, skin condition, and a breathing episode, including but not limited to heart attack, congestive heart failure, endocarditis, myocarditis, coronary artery disease, cardiomyopathy, asthma, cystic fibrosis (CF), and/or chronic obstructive pulmonary disease (COPD).

According to another embodiment, a system is provided for supporting and contactless monitoring of a person, the system comprising. The person support apparatus includes a person support surface, a movable component (e.g., a motor, deck section, bladder, etc.) configured to provide movement to the patient, and a power source configured to supply power to the person support apparatus. The person support apparatus further includes a sensing device coupled with the person support apparatus, wherein the sensing device is configured to provide a monitoring signal indicative of at least one physiological sign of a person supported on the person support apparatus without contacting the person. In addition, the person support apparatus includes a signal conditioner configured to receiving the monitoring signal and process the monitoring signal into a conditioned signal, and a data storage device receiving power from the power source and configured to store the conditioned signal as data. Moreover, the person support apparatus includes a processor powered by the powered source and configured to receive the data signal and to determine at least one of an alarm condition and the onset of an episode. The system further comprises a communication network configured to receive an indication of the alarm condition/onset. The communication network is configured to at least one of 1) record that the alarm condition/onset has occurred, 2) report to at least one personnel that the alarm condition/onset has occurred, and 3) modify an allocation of tasks or resources based on the alarm condition/onset.

In any one or more embodiments described above or described herein, a processor can be located within, connected to, or coupled with the apparatus, and configured to receive the monitoring signal and determine the onset of a physiological episode based upon the monitoring signal. The determination of the onset can be a determination that an episode is beginning to occur, or a prediction that an episode will be occurring soon. The episodes described herein may comprise various physiological episodes or events, such as those involving heart activity or breathing/lung activity or skin condition for example, including but not limited to heart attack, congestive heart failure, endocarditis, myocarditis, coronary artery disease, cardiomyopathy, asthma, cystic fibrosis (CF), and/or chronic obstructive pulmonary disease (COPD). Skin episodes that can be detected using patient movement, heart rate, and/or breath rate via the embodiments herein include skin deterioration and decubitus ulcers.

These and other features, alone or in combination with any other feature(s) (such as those described herein and/or those listed in the claims) may comprise patentable subject matter. Such features and principles of the disclosure will become apparent to those skilled in the art upon consideration of the following detailed description of various examples and embodiments illustrating the best mode of carrying out the features and principles as presently perceived.

BRIEF DESCRIPTION OF THE DRAWINGS

The detailed description particularly refers to the accompanying figures, in which.

DETAILED DESCRIPTION OF THE DRAWINGS

Figure 1:
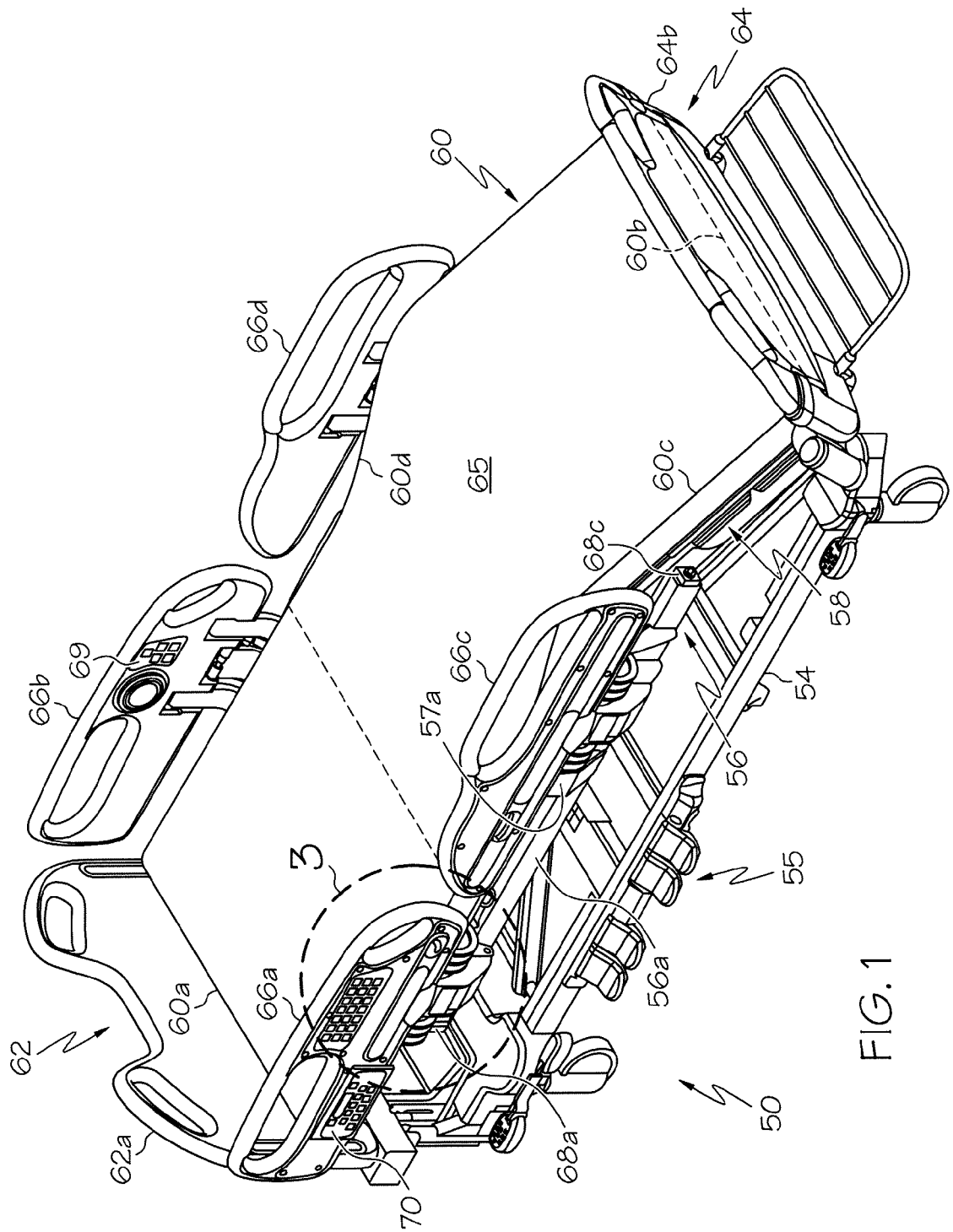
FIG. 1 is a perspective view of an embodiment of a person support apparatus according to one or more principles of the present disclosure.

In FIG. 1, one illustrative embodiment of a person support apparatus, in the form of a bed 50, is shown. The bed 50 is implemented in the context of a hospital bed generally of the type described in U.S. Pat. No. 6,208,250, the disclosure of which is incorporated herein by reference. It will be appreciated, however, that the concepts illustrated and described herein are applicable to other person support apparatuses, including for example, but not limited to, stretchers, wheelchairs, seats, chairs, or other person-supporting apparatus. Any such other systems utilizing the concepts illustrated and described herein are contemplated by this disclosure.

The illustrative hospital bed 50 of this embodiment has a bed frame which, in the illustrative example, includes a stationary base 54 coupled to a weigh frame 56 that is mounted via frame members 57a to an adjustably positionable mattress support frame or deck 58 configured to support a person directly or indirectly (e.g., via mattress 60). The mattress 60 defines a patient support surface 65 bounded by a head end 60a positioned adjacent to a headboard 62a mounted to the mattress support frame 58 at a head end 62 of the bed 50, a foot end 60b positioned adjacent to a footboard 64b mounted to the mattress support frame 58 at a foot end 64 of the bed 50, a left side 60c and a right side 60d. A pair of siderails 66a and 66c are mounted to the mattress support frame 58 adjacent to one side 60c of the mattress 60, and another pair of siderails 66b and 66d are mounted to the mattress support frame 58 adjacent to the opposite side 60d of the mattress 60. The siderail 66a supports a patient monitoring control panel 70, and the siderail 66b supports a mattress position control panel 69. The bed 50 is generally configured to adjustably position the mattress support 58 relative to the base 54.

Structures and devices can be provided to adjustably position the mattress support 58, and such structures and devices may include, for example, linkages, drives, and other movement members and devices coupled between base 54 and the weigh frame 56, and/or between weigh frame 56 and mattress support frame 58. Control of the position of the mattress support frame 58 and mattress 60 relative to the base 54 or weigh frame 56 can be provided, for example, by a patient control pendant (not shown), a mattress position control panel 69, and/or a number of mattress positioning pedals 55. The mattress support frame 58 may, for example, be adjustably positioned in a general incline from the head end 62 to the foot end 64 or vice versa. Additionally, the mattress support 58 may be adjustably positioned such that the head end 60a of the mattress 60 is positioned between minimum and maximum incline angles, e.g., 0-65 degrees, relative to horizontal or bed flat, and the mattress support 58 may also be adjustably positioned such that the thigh area 60f of the mattress 60 is positioned between minimum and maximum bend angles, e.g., 0-35 degrees, relative to horizontal or bed flat. The mattress support frame 58 or portions thereof may be adjustably positioned in other orientations, and such other orientations are contemplated by this disclosure.

Figure 2:
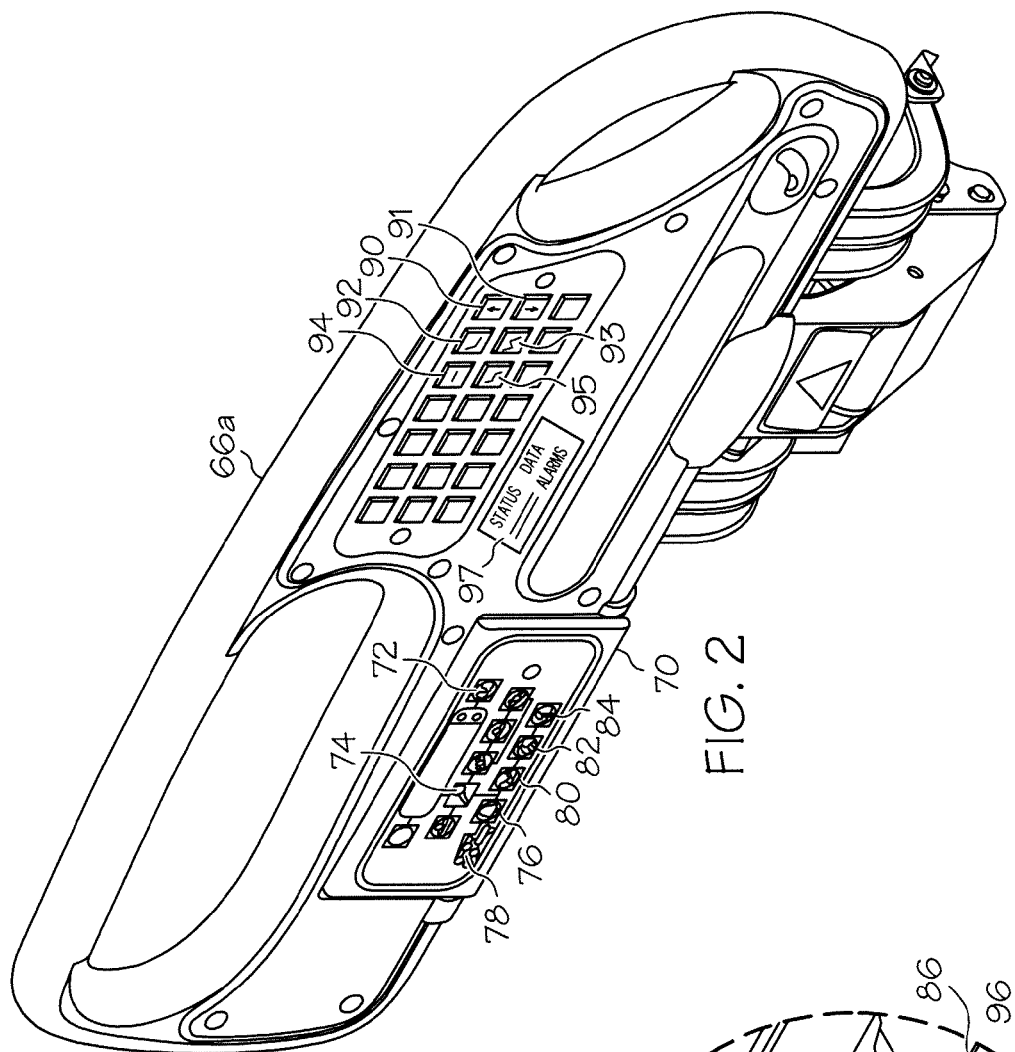
FIG. 2 is a perspective view of the siderail of the person support apparatus of FIG. 1 showing a user interface of the person support apparatus.

Referring to FIG. 2, details are shown of one illustrative user interface in the form of a control panel 70 mounted to the siderail 66a of the bed 50 of FIG. 1. The control panel 70 includes various user-interface components including, for example, a select switch 72, an enable or key switch 74, a volume control switch 76, a volume strength indicator 78, and mode switches 80-84. The mode switches 80-84 may be individually actuated to select between various patient monitoring modes. The control panel 70 illustrated in FIG. 2 includes additional switches and other components that provide for monitoring and control of other features of the bed 50. For example, the panel 70 may include a button 90 to raise all sections of the deck, a button 91 to lower all sections of the deck, a button 92 to tilt the head section of the deck up, a button 93 to tilt the head section of the deck down, a button 94 to place all deck sections flat, and a button 95 to place the apparatus in a chair position (with the head section angled up, and the foot section angled down). Other such inputs and controls can be provided. For example, a screen or touchscreen 97 can be provided to allow for inputs to control the bed or provide settings to the bed, as well as to display information to the user (such as status of various features of the bed, data regarding the bed or the patient, and/or alarms regarding the bed or the patient).

Figure 3:
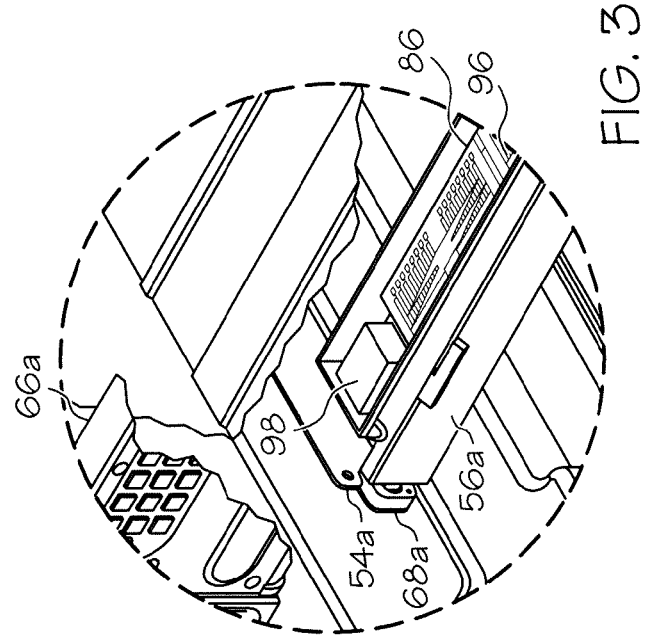
FIG. 3 is a close-up view, taken along line 3 of FIG. 1, with portions broken away, showing a processor and some of the electronics of the patient support apparatus of FIG. 1.
Figure 4:
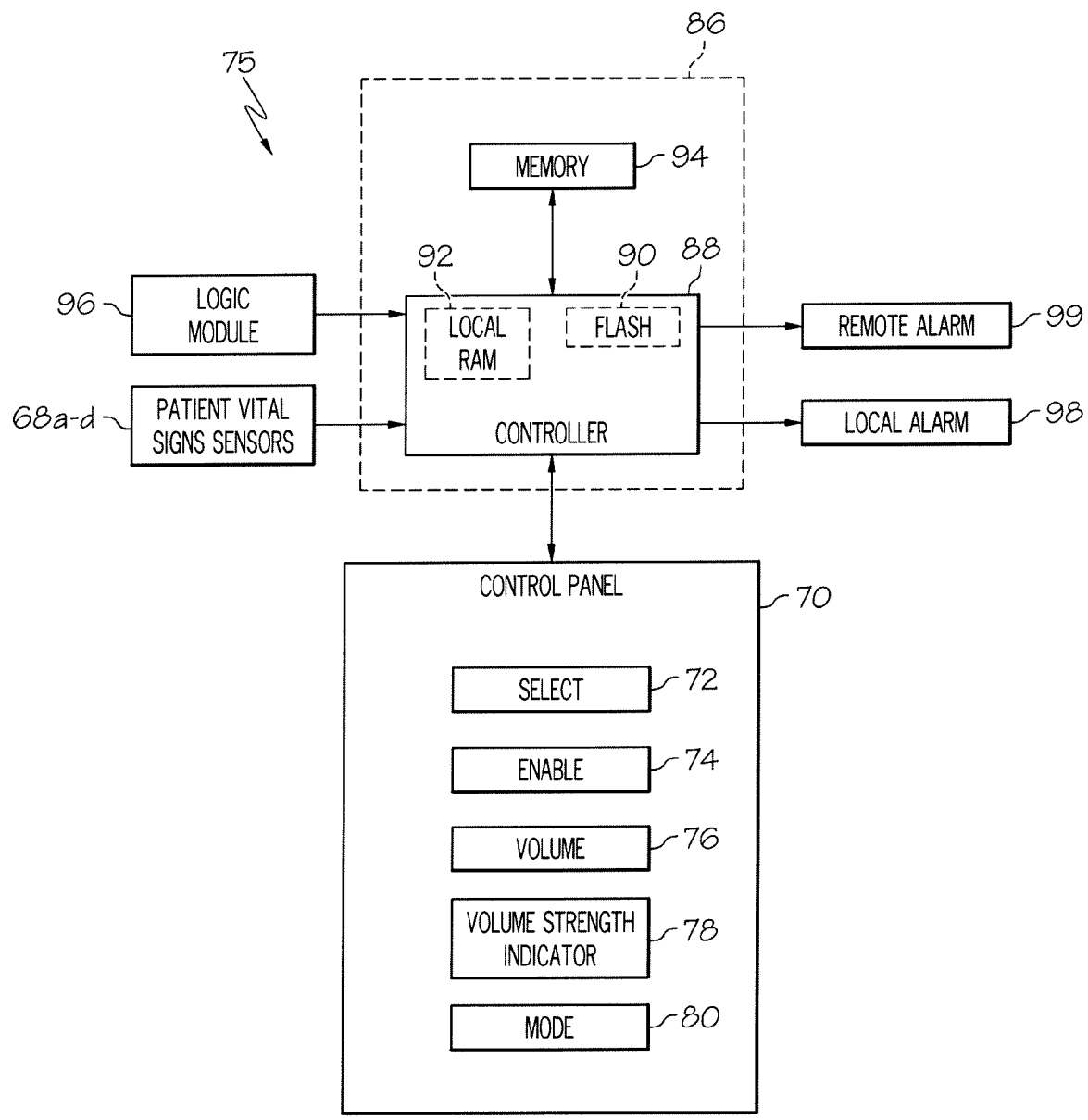
FIG. 4 is a block diagram of portions of the apparatus of the embodiment of FIG. 1.

Referring now to FIGS. 3 and 4, the right side frame member 56a of the weigh frame 56 includes a housing 56a mounted thereto adjacent to the base support frame 54a. The housing 56a is configured to carry a processor module 86 and a logic module 96 electrically coupled thereto. In the exemplary embodiment, the processor module 86 forms part of a patient monitoring system and includes a number of executable software algorithms for controlling operation of the system, and various embodiments of such a patient monitoring systems are shown in below. The patient monitoring system 75 of this embodiment includes the processor module 86 electrically coupled to the logic module 96, one or more integrated patient vital sign sensors 68a-d (described in more detail below), the control panel 70, a local alarm 98 (mounted to or situated near the bed 50) and a remote alarm 99. The remote alarm 99 is located near a caregiver or other patient monitoring individual, and is signaled by the processor module 86 to alert the remote caregiver or other patient monitoring individual via an audible and/or visual or other alarm (not shown) of certain patient activities as will be described in greater detail hereinafter.

The processor module 86 of this embodiment includes a microprocessor-based controller 88 having a Flash memory unit 90 and a local RAM memory unit 92 as shown diagrammatically in FIG. 4. The module 86 further includes an auxiliary memory unit 94, which may be an EEPROM or other conventional memory unit that is electrically connected to the controller 88. The logic module 96 and sensors 68a-d are electrically connected to the controller 88. The controller 88 is also electrically connected to the local alarm 98 and to the remote alarm 99, and the controller 88 is configured to control operation of such alarms 98 and 99. The control panel 70 is also electrically connected to the controller 88 to communicate information from the various switches and other input devices 72-76 and 80-84 from the control panel 70 to the controller 88, and to communicate information from the controller 88 to the volume strength indicator 78.

The sensors 68a-d are coupled to the bed 50 and are configured to provide a monitoring signal indicative of at least one physiological sign of a person supported on the person support apparatus without contacting the person. These sensors 68a-d may comprise piezoelectric sensors that produce a signal change indicative of the sign being monitored. Various piezoelectric materials and configurations can be utilized for such sensors, such as those described in U.S. Pat. Nos. 7,127,948; 4,889,131; and 3,996,928, just to list a few, the disclosures of each of which are hereby incorporated by referenced herein. The processor 86 is thus coupled to the bed 50 and configured to receive the monitoring signals from the sensors 68a-d. The processor 86 is protected from fluids and environment via the housing 56a, which is connected with the bed 50.

The processor 86 is also configured, via the software it runs from its logic 96, to determine the onset of a physiological sign, event, or episode of the person based upon the monitoring signal. The monitoring signal from the sensors 68a-68d may comprise at least one of a heart rate signal and a breathing signal and the physiological sign determined by the processor can comprise an adverse heart episode or breathing episode. For example, the heart episode or breathing episode, the onset which is determined by the processor 96, can be any of a number of adverse health events/conditions, such as a heart attack, congestive heart failure, endocarditis, myocarditis, coronary artery disease, cardiomyopathy, asthma, cystic fibrosis (CF), and chronic obstructive pulmonary disease (COPD). Various methods can be utilized to detect/predict the onset of such an episode, such as those described in U.S. Pat. Nos. 7,314,451; 7,077,810; and 4,422,458 and U.S. Patent Application Publication Nos. 2008/0114260 A1 and 2007/0118054 A1, for example, the disclosures of each of which are incorporated by reference herein. Such a detection or prediction can be achieved by comparing the heart rate and/or breath rates to various patterns stored in memory, and determining whether the measured heart rate and/or breath rate matches a pattern that is associated with the onset of a condition. As an alternative, this can be achieved by a set of rules that has threshold levels of heart/breath rate, amplitude and changes in the same which correspond with various conditions. If the currently measured signals match such a rule, then the processor 86 indicates that the onset of the condition is occurring or is about to occur, such as by sounding or lighting an alarm on control panel 70, or otherwise communicating with the caregiver and/or patient. The patterns or rules which are compared to the heart or breath rate detected by the sensors 68a-d can be established by analyzing heart and breath rate of a population of patients having the onset of various episodes. The current data from the sensors 68a-d can thus be compared to such patterns or rules to determine whether an onset is occurring or is about to occur. Alarms and data from this monitoring can be displayed via the displays and indicators on sidereal 66a (FIGS. 1 and 3), and the controls/inputs on this siderail can be used to select parameters for the monitoring, enable the monitoring, select the mode of the monitoring, and adjust the volume of the monitoring (e.g., via controls 72, 74, 78, 78, and 80). Additionally, these controls can be used to control other functions of the bed (such as the bed height and movement and articulation), as described above with respect to buttons 90, 91, 92, and 94.

Figure 5:
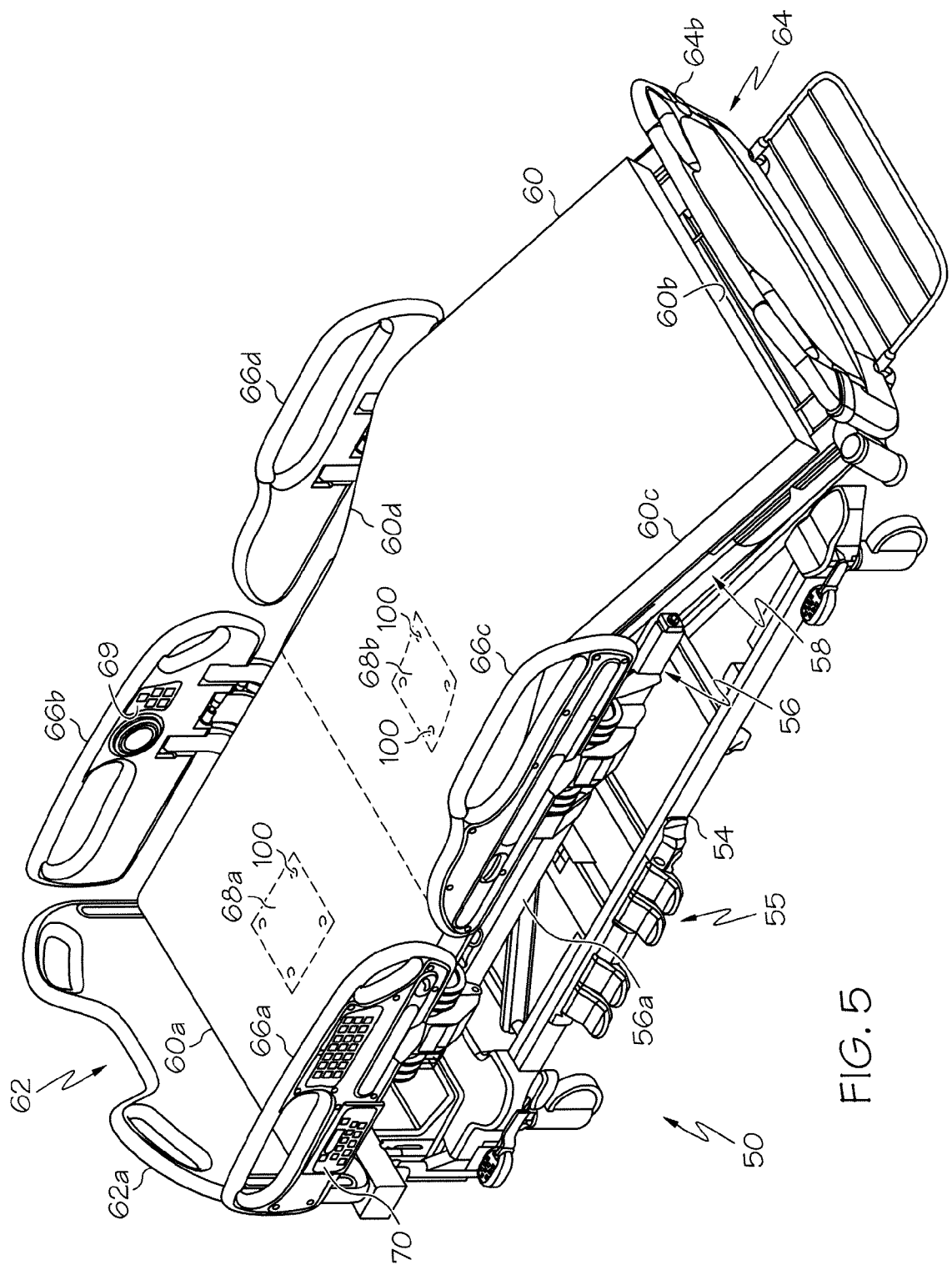
FIG. 5 is a perspective view of another embodiment of a person support apparatus according to one or more principles of the present disclosure.

FIG. 5 illustrates alternative or additional locations for the sensors 68a, 68b. In this embodiment, two sensing devices 68a and 68b are coupled to the bed 50 or mattress 60. These sensing devices 68a and 68b can be attached directly to the top of the deck 58 such as via one or more connectors 100, which can comprise bolts, screws, pins, welds, and the like. Thus, a tool can be required for removable of the sensing devices 68. For example, if the sensing device is bolted to the deck, then a wrench may be required for its removal; if the sensing device is screwed to the deck, then a screwdriver may be required for its removal; and if the sensing device is welded to the deck, then welding equipment might be required for its removal. Additionally or alternatively, an adhesive may be used to fix sensors 68a, 68b in place on the deck 58.

In one embodiment, if multiple sensors are utilized, one sensor 68a can be affixed to a head deck section below where the patient's torso generally would be located and the other sensor 68b can be affixed to a seat deck section below where the patient's mid section or seat section would generally be located. Accordingly, in the example of FIG. 5, one sensor 68a is affixed to the head section of the deck 58 and one sensor 68b is affixed to the seat section of the deck 58, to monitor the pressure changes at both locations. The sensors 68a and 68b can be any of a variety of suitable sensors, such as pressure sensors, transducers, sensors that produce an output based upon change of pressure or movement on the bed 50, or other sensors sensitive to the physiological functioning or condition of the patient such as the piezoelectric sensors mentioned above.

Figure 6:
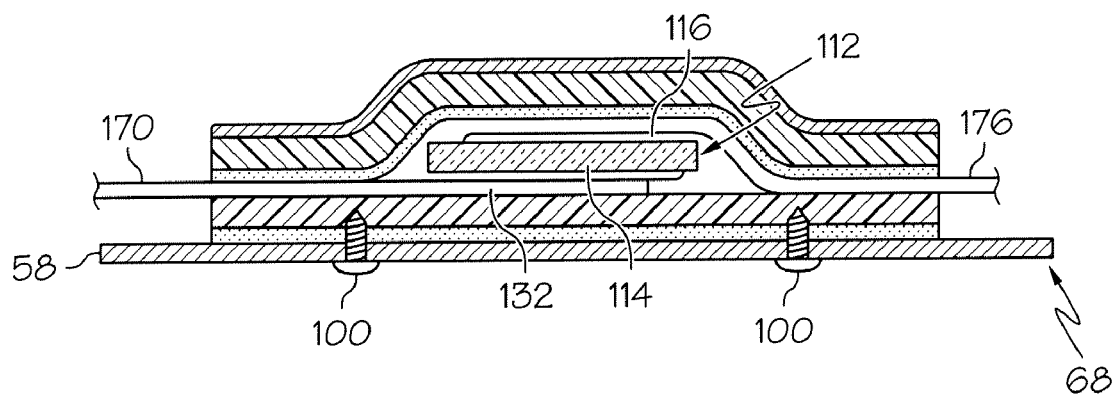
FIG. 6 is a side view of a sensor embodiment that can be used with some of the patient support apparatus embodiments disclosed herein according to principles of the present disclosure.
Figure 7:
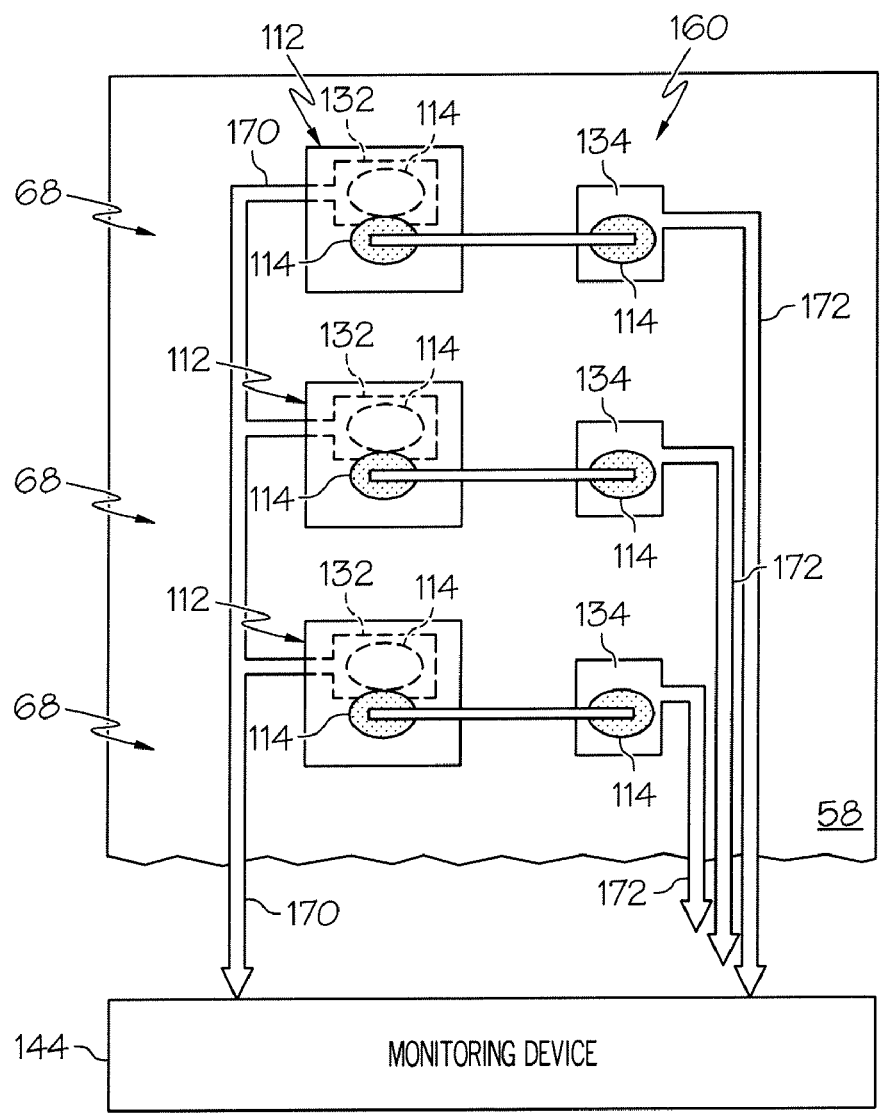
FIG. 7 is a top view of an array of sensors that can be used with some of the patient support apparatus embodiments disclosed herein according to principles of the present disclosure.

FIGS. 6-7 show examples of types of sensors 68 that could be utilized in any of the embodiments described herein, if desired. The sensors 68 could be attached to the deck 58 individually, or in an array 160 (if multiple sensors are used). In this example, each piezoelectric sensory device 112 in each array 160 is electrically connected to terminals 132, 134 so that the electric potential between the contacts of each sensory device 112 can be detected by measuring the electric potential between the respective terminals 132, 134. In some cases, some or all of the first terminals 132 of each array 160 are electrically connected to one another so that the first contact surfaces 114 of several or all of the piezoelectric sensory devices 112 are connected. However, the second terminals 134, which are connected to the second contact surfaces 116 of the piezoelectric sensory devices 112, are electrically separate in such an embodiment. The monitoring device 144 can be electrically connected to each of the first contact surfaces 114 via a single electrical connection to the first terminals 132, and the device 144 can be separately connected to each of the other terminals 134. Thus, the device 144 can detect the electric potential between each terminal 134 and the first terminal 132, to thereby determine the pressure at the position of each sensor 68.

The array 160 can be disposed on the deck 58 of the bed 50 so that the various piezoelectric sensory devices 112 are provided at a plurality of positions. For example, each array 160 can extend in a direction between the head and foot ends of the deck so that each array 160 can be used to detect a pressure profile between the head and foot ends. In fact, the sensors 68, or arrays 160 of sensors 68, can be disposed on any portion of the deck 58 and on any combination of portions of deck 58, depending on the positions for which pressure measurement (and ultimately patient condition) is desired.

Each sensor 68 is thus configured to provide a monitoring signal indicative of at least one physiological sign of a person supported on the person support apparatus without contacting the person. Variations in pressure provided by the sensor 68 represent heart rate or breath rate, and can thus be processed accordingly. For example, various filtering algorithms can be used to filter out unwanted incoming data with the filtered data being representative of the patient's heart beats and breathing patterns. Returning again to FIGS. 1-5, the processor 86 is thus coupled to the person support apparatus and configures to receive the monitoring signal and to determine the onset of a physiological sign of the person based upon the monitoring signal.

Figure 8:
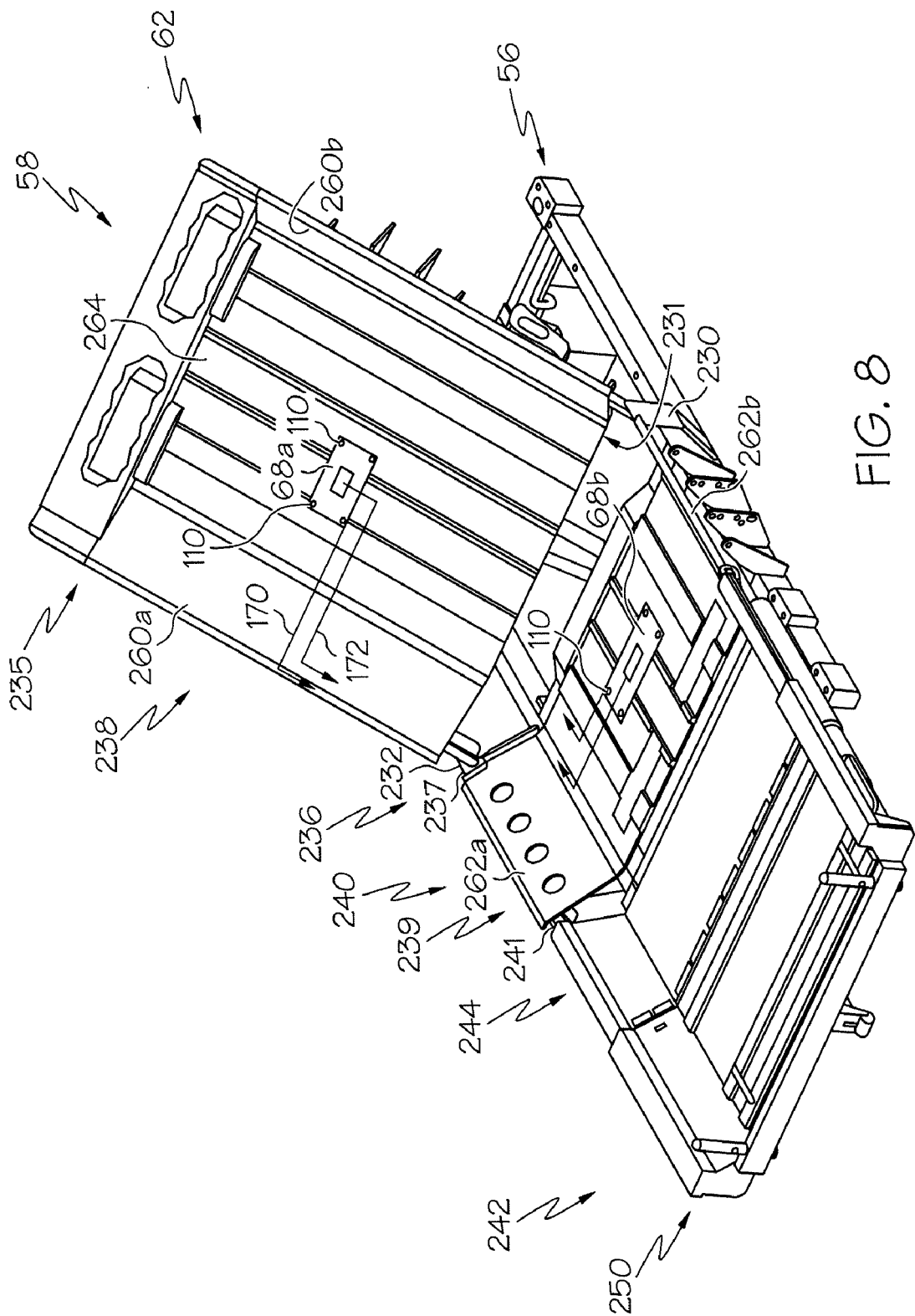
FIG. 8 is a top perspective view of an upper frame and mattress support deck of a person support apparatus according to one or more principles of the present disclosure.
Figure 9:
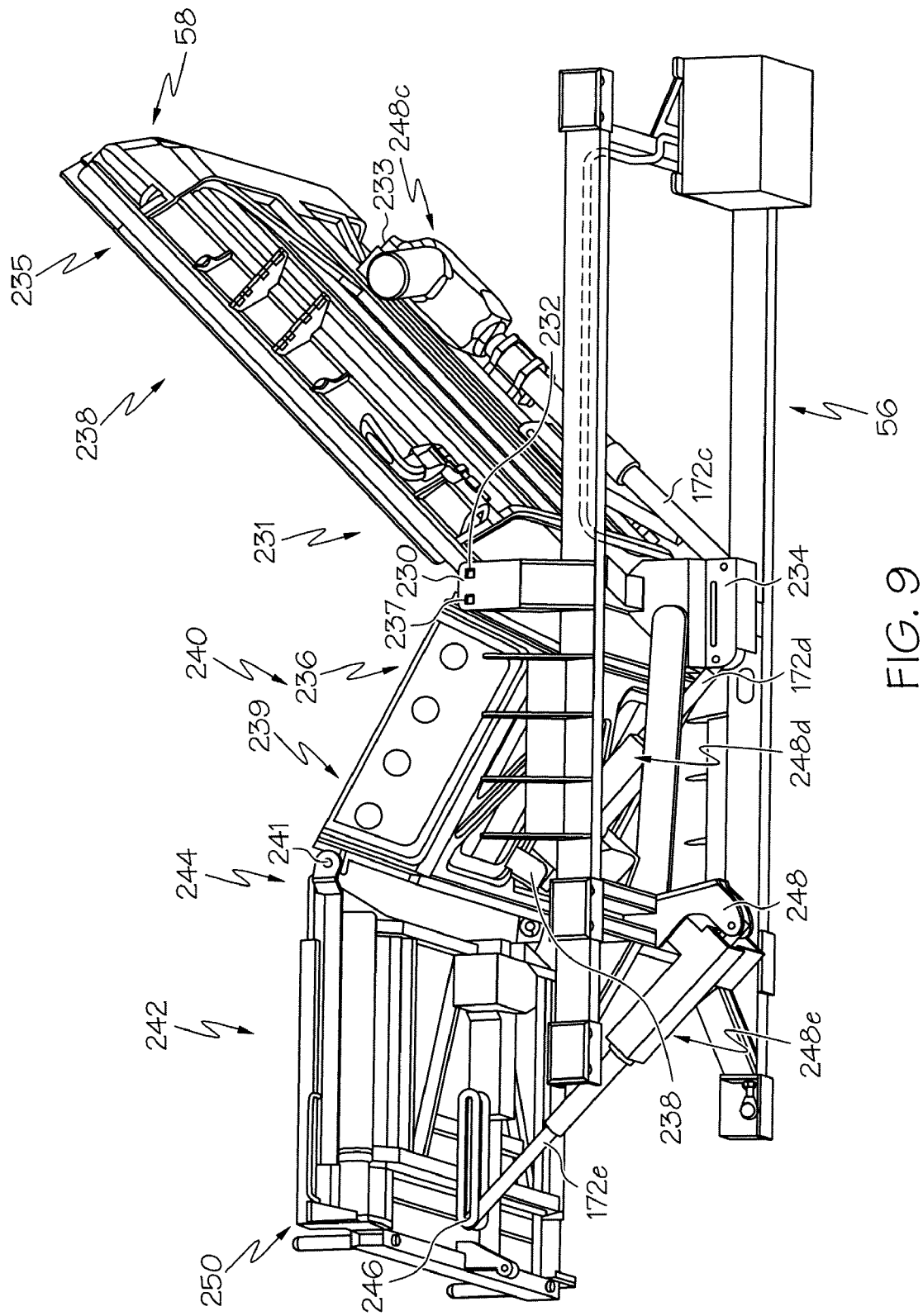
FIG. 9 is another perspective view of the upper frame and mattress support deck of the embodiment of FIG. 8.

As shown in FIGS. 1-5 and as previously mentioned, deck 58 is coupled to weigh frame 56. FIG. 8 shows an embodiment in which the deck 58 includes several sections 238, 240, 242 that are configured to articulate between a plurality of positions. Head section 238 is positioned adjacent headboard 62a (FIG. 1) and is pivotably coupled to weigh frame 56. In the illustrated embodiment as shown in 8, a first end 231 of head section 238 is pivotably coupled to upwardly extending flanges 230 of weigh frame 56 such that head section 238 is rotatable about a pivot 232. Head section 238 is further coupled to actuator 248c. In this illustrated embodiment, and as shown in FIG. 9, actuator 248c is pivotably coupled to a downwardly extending bracket 233 of head section 38 and to a bracket 234 of weigh frame 56. Actuator 248c is configured to raise a second end 235 of head section 238. As such, second end 235 of head section 238 can be raised or lowered relative to first end 231, by the extension or retraction of the length of cylinder 172c of actuator 248c.

In this embodiment, seat section 240 of the deck is positioned adjacent head section 238 and is pivotably coupled to weigh frame 56. However, embodiments in which seat section is fixed relative to frame 56 are contemplated by this disclosure. In the illustrative example, a first end 236 of seat section 240 is pivotably coupled to flanges 230 of weigh frame 56 such that seat section 240 is rotatable about a pivot 237. Seat section 240 is further coupled to actuator 248d. In the illustrated embodiment, actuator 248d is pivotably coupled to a downwardly extending bracket 238 of seat section 240 and to bracket 234 of weigh frame 56. Actuator 248d is configured to raise a second end 239 of seat section 40. As such, second end 239 of seat section 240 may be raised or lowered relative to first end 236, by the extension or retraction of the length of cylinder 172d of actuator 248d.

In this embodiment shown in FIGS. 8 and 9, leg or foot section 242 is positioned adjacent seat section 240 and is pivotably coupled to seat section 240. Second end 239 of seat section 240 is pivotably coupled to a first end 244 of leg section 242 such that leg section 242 is rotatable about a pivot 241. Leg section 242 is further coupled to actuator 248e. In the illustrated embodiment, actuator 248e is slidably coupled to a bracket 246 of leg section 242 and is pivotably coupled to a bracket 248 of weigh frame 56. Actuator 248e is configured to raise a second end 250 of leg section 242. As such, second end 250 of leg section 242 can be raised or lowered relative to first end 244, by the extension or retraction of the length of cylinder 172e of actuator 248e.

Deck 58 is configured to support mattress 60 (as shown in the embodiments of FIGS. 1 and 5). In the deck embodiment of FIG. 8, head section 238 and seat section 240 each includes angled side walls 260a, 260b and 262a, 262b, respectively. Further, head section 238 and seat section 240 each includes substantially flat lower deck portions, floors or walls 264 and 266 connected to side walls 260a, 260b and 262a, 262b, respectively. Angled side walls 260a, 260b and floor 264 and angled side walls 262a, 262b and floor 266 each cooperate to define a support surface for a portion of mattress 60. As shown in FIG. 8, the angled walls 260a, 260b and 262a, 262b are oriented to form obtuse angles with their respective floors 264 and 266. In one illustrative embodiment, the angle formed is approximately 135 degrees. According to alternative embodiments of the present disclosure, the obtuse angles between the side walls and the floor may range from slightly more than 90 degrees to slightly less than 180 degrees. According to other alternative embodiments of the present disclosure, the angles are right angles or acute angles. Decks like deck 58 of FIG. 8 are sometimes referred to as step decks.

The lowered central portion, generally corresponding to floors 264 and 266 of head section 238 and seat section 240, respectively, provides ample space for mattress 60 to be positioned. By having a lowered central portion, the pivot of a patient's hip when the patient is positioned on mattress 60 is more in line with pivots 232, 237 of head section 238 and seat section 240 and provides ample space to provide a mattress 60 that provides adequate support for the patient. In one illustrative embodiment, the position of the pivot of the hip of the patient is about two inches above the pivots 232, 237 of the head and seat sections 238 and 240 of the deck 56. In another illustrative embodiment, the position of the pivot of the hip of the patient is generally in line with the pivots 232, 237 of the head and seat sections 238 and 240 of the deck 56. By minimizing the distance between the pivot of the patient's hip and the pivots 232, 237 of the head and seat sections 38 and 40, the amount of shear exerted against the patient is reduced as either the head or seat 238, 240 section is raised or lowered. By reducing the amount of shear exerted against the patient, the possibility of the patient experiencing skin breakdown is reduced. However, other bed and deck structures than those illustrated in FIGS. 8 and 9 can be utilized, such as flat decks (Rather than the step decks shown in FIGS. 8-9). Moreover, additional details on such embodiments can be found in U.S. Pat. No. 7,406,731, the entire disclosure of which is hereby incorporated by reference herein.

In the example of FIG. 8, two sensors 68a and 68b are attached to the deck 56. In this example, the sensors 68a and 68b are attached on top of the head section 238 and seat section 240 respectively. These sensors could thus be manufactured with the deck 56, but rest under the mattress 60. Accordingly, a signal representing a physiological condition of the patient can be obtained for the patient's torso from sensor 68a and a signal representing the physiological condition of the patient can be obtained from the patient's seat or mid section from sensor 68b. An appropriate algorithm or algorithms can then be utilized to obtain the patient's vital signs or other physiological sign(s) from these sensor signals. For example, the two signals could be averaged. Alternatively, one signal could be given priority over the other, based upon the strength of the signal, the patient's weight profile (such as determined by sensors 68a-d of FIG. 1), and/or the current status of the bed (e.g., which sections are flat and which are angled). The deck sections 238 and 240 along with their corresponding sensors affixed atop thereof thus define a support surface which supports the person (indirectly) via the mattress 60.

Figure 10:
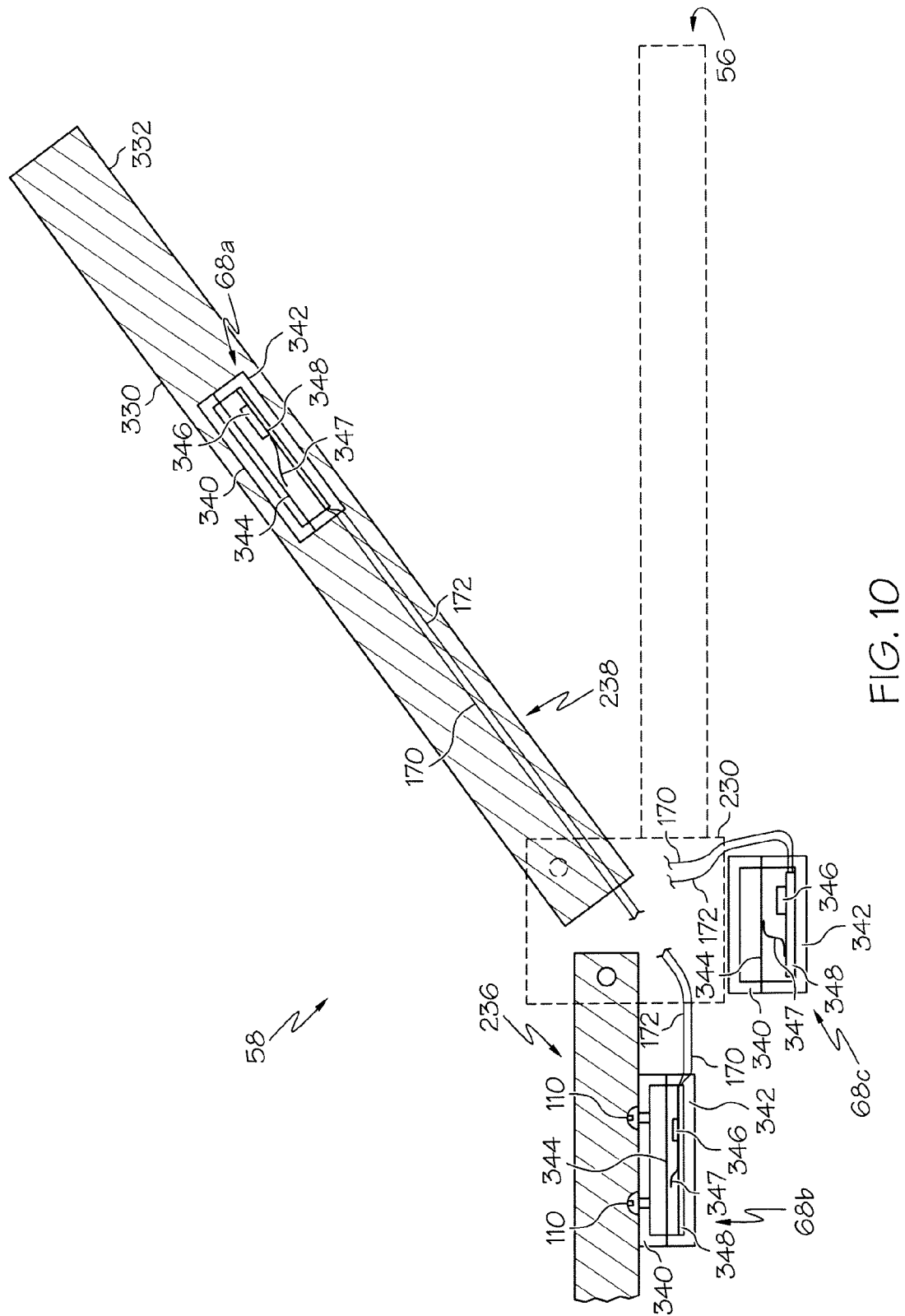
FIG. 10 is a cross-sectional side view of a person support apparatus embodiment according to one or more principles of the present disclosure.

FIG. 10 illustrates another embodiment wherein the sensor 68a is embedded within the deck 58 itself. In this embodiment, shown in cross-section schematic, the sensor 68a is embedded between the top surface 330 and bottom surface 332 of the head section 238. Accordingly, the sensor is below the frame's plane 330 which is primarily responsible for supporting the patient (indirectly in this case, via the mattress). The material from which the deck section 238 is made can be a variety of materials. For example, a fiberglass, plastic, or a composite material may be utilized, such that the sensor 68a may be molded into the deck section via a suitable molding process. For example, injection molding, insert molding, fiberglass molding, pultrusion, and/or fiberglass layering processes may be utilized to manufacture the deck portion with its embedded sensor 68a. If insert molding is utilized for example, a custom-built mold having the shape of the deck 238 is loaded (manually or robotically) with the sensor insert 68a and its attached conductors 170 and 172. The molten material is then injected into the mold or otherwise applied to the portion or cavity of the mold corresponding to the deck shape. Upon cooling, the deck 238 with embedded sensor 68a is removed from the mold. Testing of the deck section 238 and its embedded sensor 68a and its connectors 170/172 can then take place and the system can then be assembled with the remainder of the bed components. Sensors 68 can be embedded in other deck sections in a similar manner, if desired. Furthermore, multiple sensors 68 can be embedded in the same deck section, if desired.

In accordance with another embodiment, the head deck 238 is under compressive stress or tensile stress, at least when a person is not supported by the person support apparatus. Stress beams can be located at least partially in the head deck 238 and configured to provide a tensile or compressive stress to the panel. In some embodiments, the sensing device 68a is integrally molded into the panel during a molding process that creates the stress in the head deck section 238. Thus, the sensing device can comprise a piezoelectric element coupled to the head deck and placed under stress by the stress of the head deck, in some embodiments.

In the illustrative embodiment, the sensor 68a comprises a top housing 340 and a bottom housing 342 which hold therebetween a piezoelectric diaphragm member 344 in tension or stressed state. A circuit board 348 is situated inside a cavity defined by top and bottom housings 340, 342 and receives the signals representing changes in pressure via a contact spring member 347. An amplifier 346 on the circuit board 348 amplifies the signal received. Other appropriate piezoelectric processing, filtering or detecting circuitry and software or firmware may be provided on the circuit board 348. The board 348 then provides an output signal via conductor 172, which is provided to the main processor of the bed, such as processor 86 of FIG. 1 for example.

In this example, an additional sensor 68b is connected to the seat portion 236 via connectors 110. This sensor 68b has the same construction as sensor 68a of FIG. 10, and likewise provides its signal output via its respective conductor 172 to the bed processor. Accordingly, in this example, the sensor 68b is below the deck and below the plane of the bed frame's person (i.e., mattress) contacting surface. While various mounting positions and methods are described herein, others are also possible. For example, the sensors may be mounted to the frame components 56 beneath the deck 58. In this example, another sensor 68c of similar construction is mounted to the pivot plate 230 of the frame 56. This sensor can be utilized in addition or as an alternative to the other sensors shown. However, it should be noted that sensor 68b could be a different type of sensor than piezoelectric sensor 68a. For example, the sensor 68b could be one or more existing or additional load cells or inductance based sensors on the frame. In such an embodiment, the sensors determine the patient weight and/or location. In this manner, the patient weight and/or location can be utilized along with the signal from sensor 68a to best determine the physiological parameter under consideration. The weight or location can be utilized in other manners as well, such as to turn sensor 68a and/or 68c on or off, to modify the performance of these sensors 68a, 68c, to provide the patient weight to the caregiver, and/or to determine when the patient has exited or is about to exit the bed. U.S. Pat. No. 7,253,366 (load cell based bed exit system) and U.S. Pat. No. 6,067,019 (capacitive sensor based bed exit system), the entire disclosures of which are hereby incorporated by reference herein, includes descriptions of bed exit systems and methods that could be used in combination with the sensors 68 disclosed herein, if desired.

Figure 11:
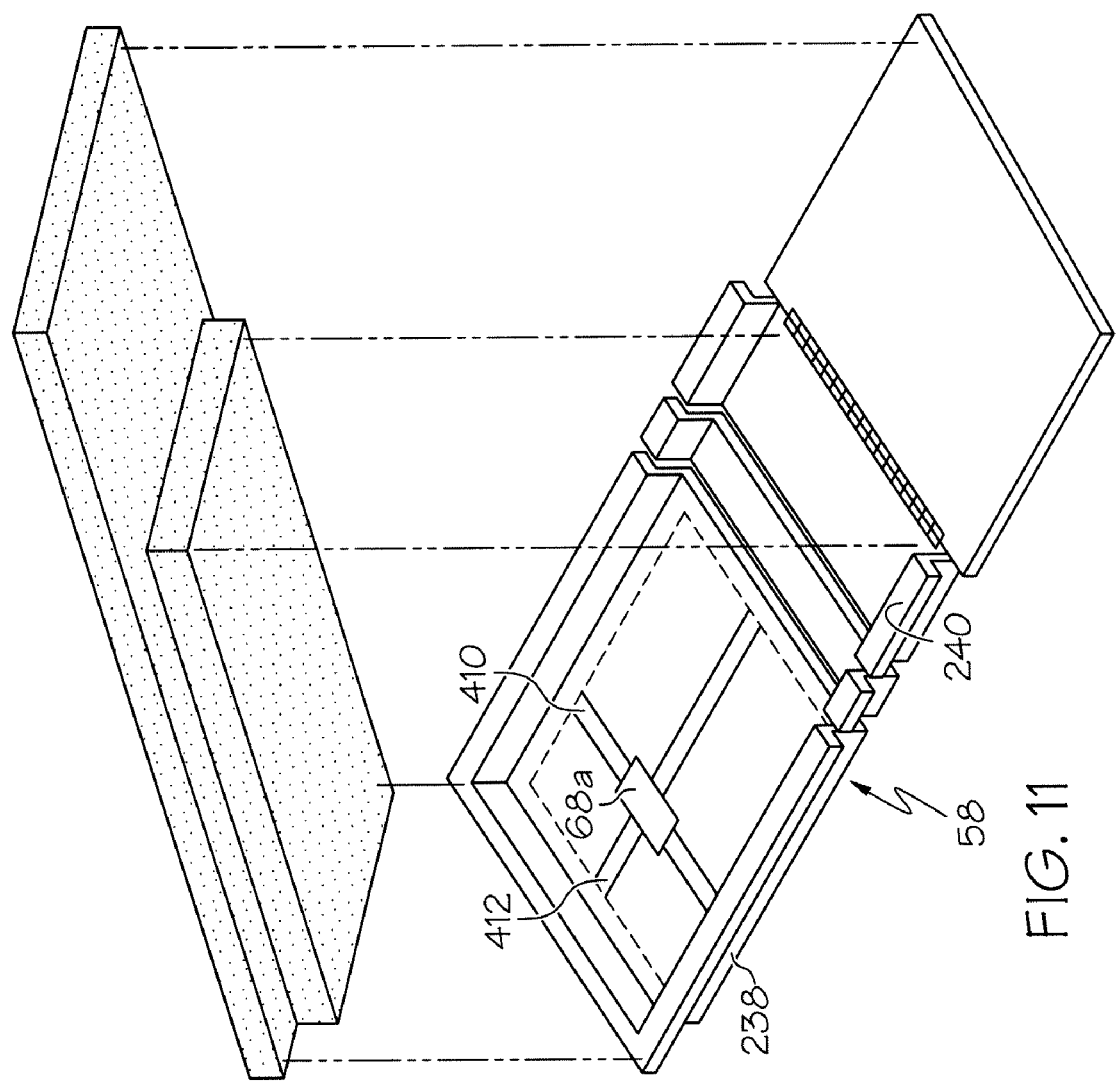
FIG. 11 is a top perspective view of a mattress and a mattress support deck of a person support apparatus embodiment according to one or more principles of the present disclosure.

Turning now to the embodiment of FIG. 11, a deck 58 is provided having a head section 238 and a seat section 240. A sensor 68a is provided near the center of the head section 238. This sensor 68a can be provided atop the head section or embedded in the head section, such as has been described earlier. Beams or waveguide members 410 and 412 are provided on or in the deck section 238, to provide support to the deck section and/or to allow for transmission of forces from outside the sensor 68a to the sensor. Such beams 410, 412 can be made of suitable materials for transmitting energy such as mechanical forces or pressure changes, caused by the patient, along the deck to the sensor 68a, such as metal strips, wires, mattress support straps, or the like. Such an arrangement can assist in ensuring that the pressure changes caused by the patient (e.g., via the patient's heart beat or breathing) are transmitted to the sensor, even if the patient is not perfectly positioned over the sensor. Such beams or waveguides 410, 412 could alternatively comprise stressed piezoelectric material that is coupled with the piezoelectric material in the sensor 68a, for example. The waveguides 410, 412, alternatively or additionally, may comprise acoustic waveguides, such as members having channels or tunnels provided therein, that direct sound waves to an acoustic sensing device of sensor 68a. Deck section 240 may have similar types of waveguides 410, 412 in some embodiments.

Figure 12:
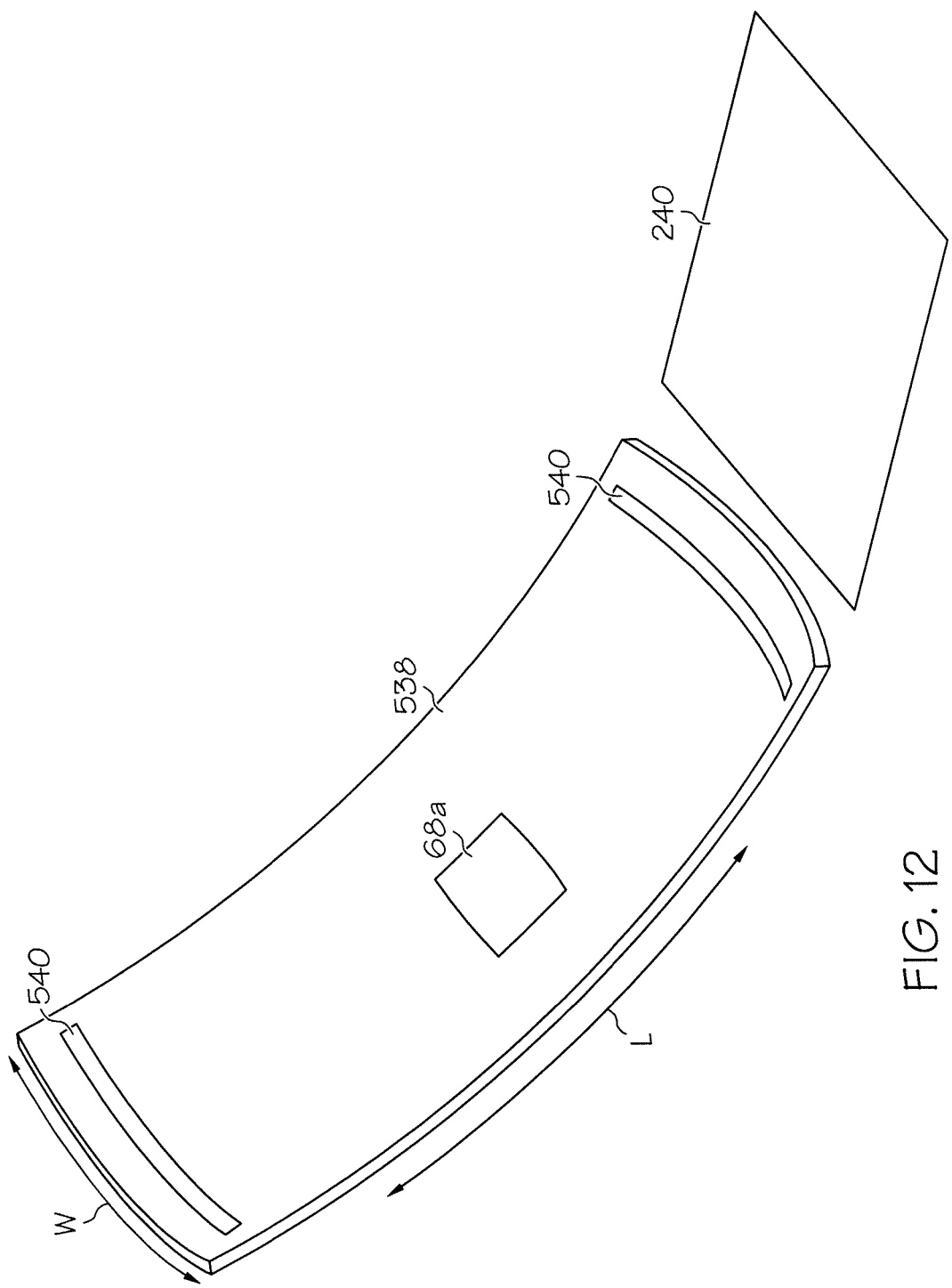
FIG. 12 is a top perspective view of a portion of a mattress support deck of a person support apparatus embodiment according to one or more principles of the present disclosure.

FIG. 12 illustrates yet another embodiment of a deck section 538 according to this disclosure. In this example, the head deck section 538 is curved or nonlinear in both its width dimension "w" and its length dimension "l." Accordingly, forces have a tendency to be transmitted toward, or concentrated at, the center region of the section 538, where a sensor 68a is mounted or is embedded. This shape of the head deck section 538 provides a non-planar support surface. In this example, support beams 540 are embedded or attached to the section 538 to provide additional strength and rigidity. However, these beams are further from the center of the section than is the sensor 68a. The section 538 can take on a number of nonlinear or nonplanar shapes in one or more dimensions or at one or more locations, such as curved shapes, parabolic shapes, dish shapes, bowl shapes, and the like. Such shapes can be provided to assist in directing of forces or pressures created by the patient toward the sensor 68a. They can be directed toward the sensor 68a without passing through any beam 540, so as to reduce attenuation of these forces. As mentioned above, the signals picked up by the sensor 68a can be detected and used to determine heart rate, breathing rate, patient condition and the like, and/or to predict or to recognize the onset of an adverse heart episode, breathing episode, skin episode, or other such condition or event adverse to the patient being supported by the deck section 538. As with the other embodiments described herein, such episodes which are detected based on outputs of sensors 68 could comprise heart attack, congestive heart failure, endocarditis, myocarditis, coronary artery disease, cardiomyopathy, asthma, cystic fibrosis (CF), and/or chronic obstructive pulmonary disease (COPD). Skin episodes that can be detected using patient movement, heart rate, and/or breath rate via one or more of the embodiments herein include skin deterioration and decubitus ulcers. In such embodiments, the heart rate and/or breath rate can be correlated to a metabolic rate, and the metabolic rate used to detect when the skin episode may occur. The motion of the patient can be utilized in combination of one or more of the heart rate, breath rate, and metabolic rate to confirm the presence of the skin episode and/or the onset of the skin episode.

Figure 13:
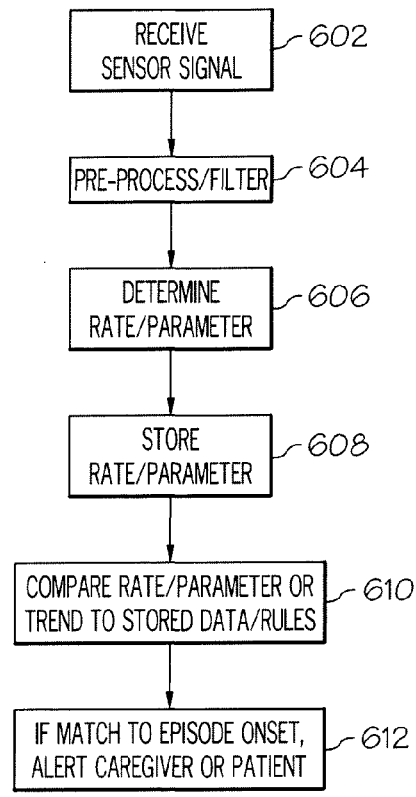
FIG. 13 is a flow diagram of an embodiment of a signal processing and alarming method for use with one or more embodiments herein according to principles of the present disclosure.
Figure 15:
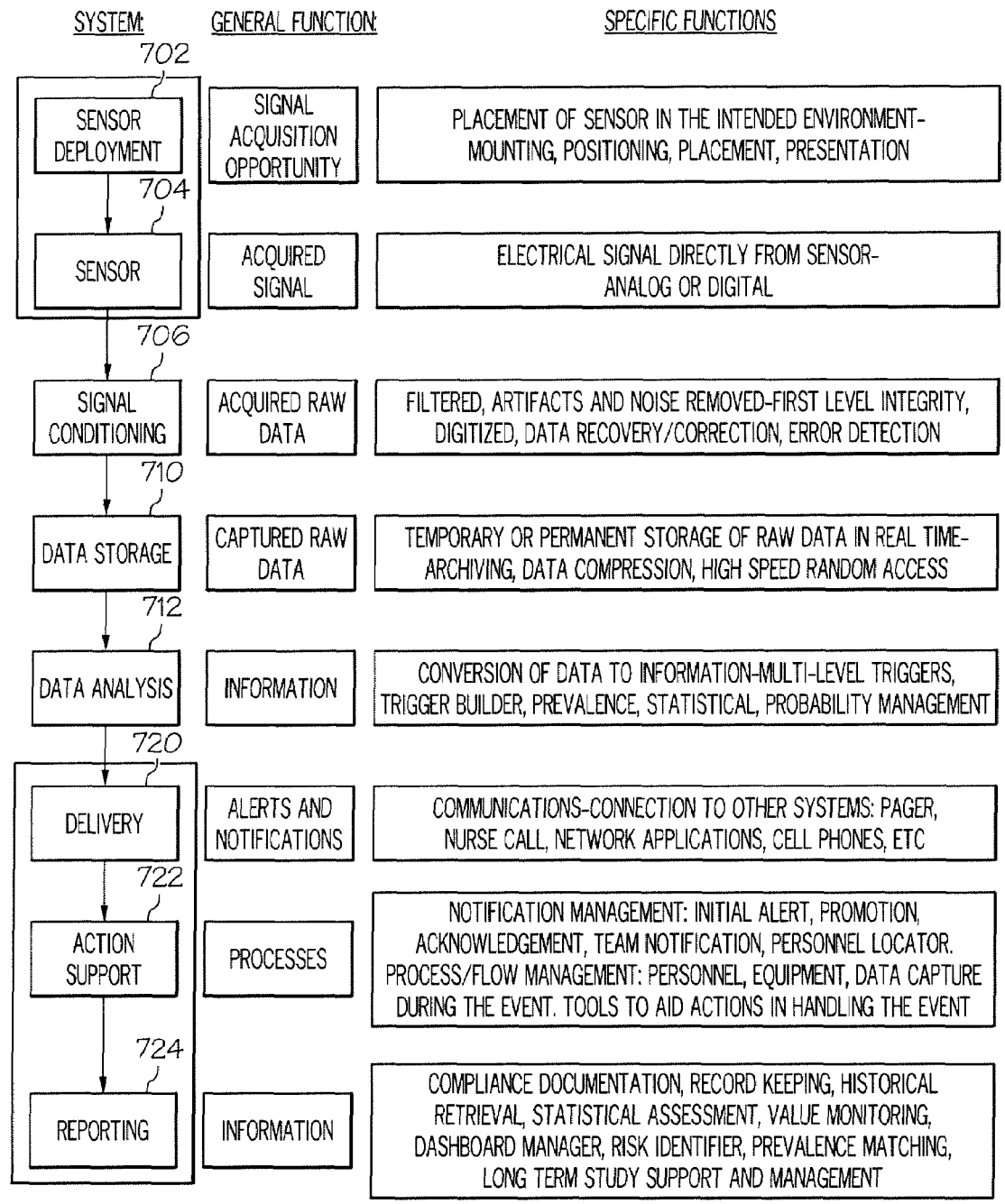
FIG. 15 is a block diagram of a system according to one embodiment and which may be used with one or more embodiments herein according to principles of the present disclosure.

FIG. 13 is a flow diagram of a method that can be utilized to detect patient parameters and to detect the onset of a condition, according to some embodiments. Such a method can be utilized in conjunction with one or more of the embodiments described herein. This embodiment and the embodiments above can be part of a larger system, such as shown in FIG. 15. With reference to FIGS. 13 and 15, the sensor signal, such as from sensor 68, is received, at step 602. The signal from the sensor is in its raw format, as either an analog or digital signal. It is obtained by deploying sensors 704 (e.g., sensor 68 described above) via the sensor deployment elements 702 (e.g., the person support apparatuses, decks, frames, connectors, described above) as suggested in FIG. 15. The signal is then pre-processed, such as by filtering and/or conditioning, as shown at step 604 of FIG. 13, such as by signal conditioning elements 706 of FIG. 15. This step can entail filtering and removing artifacts and noise, correcting erroneous data, or correcting errors. Various components can be utilized for such operations such as analog or digital filters and signal processors, amplifiers, and analog-to-digital converters.

The conditioned data is then stored, as shown at step 608 of FIG. 13, and such as via data storage elements 710 as shown in FIG. 15. Such elements can conduct temporary or permanent storage of the data in real time or substantially real time, and can conduct other processes such as compressing the data, allowing for faster access of the data, and/or archiving the data.

Figure 14:
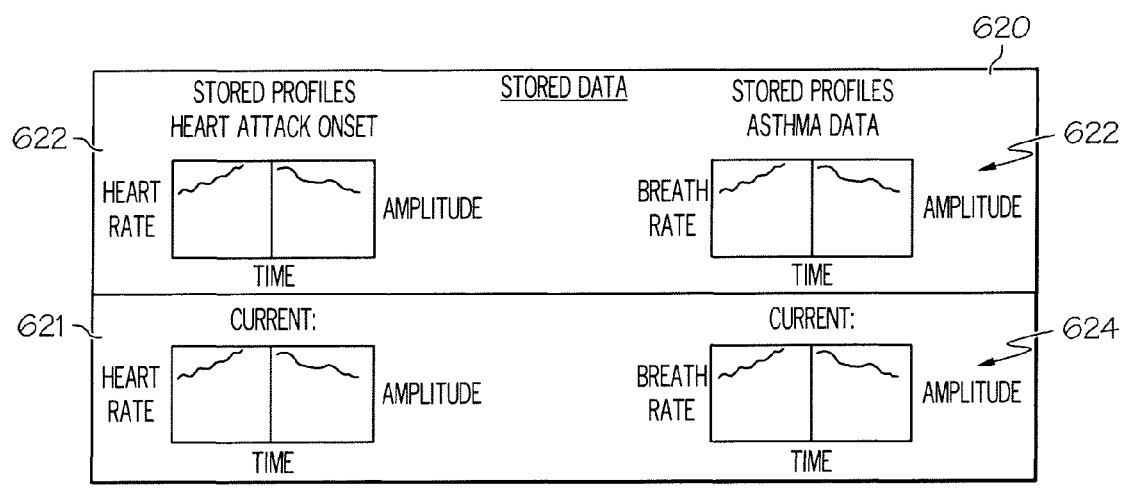
FIG. 14 is a schematic diagram of an embodiment of stored data for use with one or more embodiment herein according to principles of the present disclosure.

The data is then compared to historical data, of the patient or of the population in general or of the patient's specific demographic. In the example of FIG. 13, this entails comparing the rate determined (e.g., the heart rate or breath rate) to what is expected (or to what is not expected). Alternatively or additionally, this can entail comparing the trend of the parameter (its rate of change or other function of the parameter) to what is/is not expected. This is shown at step 610 of FIG. 13 and can be carried out by the data analysis system elements 712 shown in FIG. 15. Such elements can convert the data into useful information by comparing to triggers, and performing statistical or probability analysis on the data. Processors, such as programmed computers, microprocessors, controllers and other circuitry can carry out such analysis. Such analysis can be carried out, for example, by comparing current patient heart or breath rate and amplitude trends over time, shown on graph 621 of FIG. 14, to historical data, shown on graph 622 of FIG. 14, on rates and amplitudes that has been deemed to be problematic (or to indicate the occurrence or onset of an episode). Examples of various methods for performing such analysis are described in U.S. Pat. Nos. 7,077,810; 5,101,828; 7,306,564; 7,183,930; 7,304,580; 6,984,207; and 7,314,451 and in U.S. Patent Application Publication No. 2007/0118054, the entire disclosures of which are hereby incorporated herein by reference.

If it is determined that an episode is occurring, then the data analysis elements 712 of FIG. 15 create an alert or otherwise notify the desired persons. This is shown at step 612 of FIG. 13.

The data and/or any alarms or alerts can then be reported out to appropriate persons or equipment. This can be conducted by the system elements 720, 722, and 724 shown in the embodiment of FIG. 15. First, it may be desirable to deliver the data and/or notification of any episode or episode onset to appropriate personnel, such as via pagers, nurse call systems, computer networks, cell phones, and other communication devices. This is shown at block 720 of FIG. 15. Then, it can be desirable to place multiple persons into action to deal with the data/episode/onset. Here, software and hardware tools can be utilized to promote an alert to the next person if it is not acknowledged by the first person, to locate personnel that can respond to the alert (e.g., by tracking or task management software), to deploy the correct equipment to the site of the patient, and to otherwise aid in handling the event. Patient and/or task flow software can be utilized for this purpose. U.S. Pat. Nos. 7,319,386; 7,242,306; 7,315,535; and 7,248,933, and U.S. Patent Application Publication 2005/0168341, the entire disclosures of which are hereby incorporated herein by reference, provide examples of nurse call, patient flow, and asset tracking systems that could be utilized to assist in this purpose. Such elements are shown at block 722 of FIG. 15. Additionally, the data and alerts/alarms can be recorded such as for compliance documentation, record keeping, historical retrieval (e.g., electronic medical records), risk identification, and the like. These system elements of this embodiment of FIG. 15 are shown at block 724.

Figure 16:
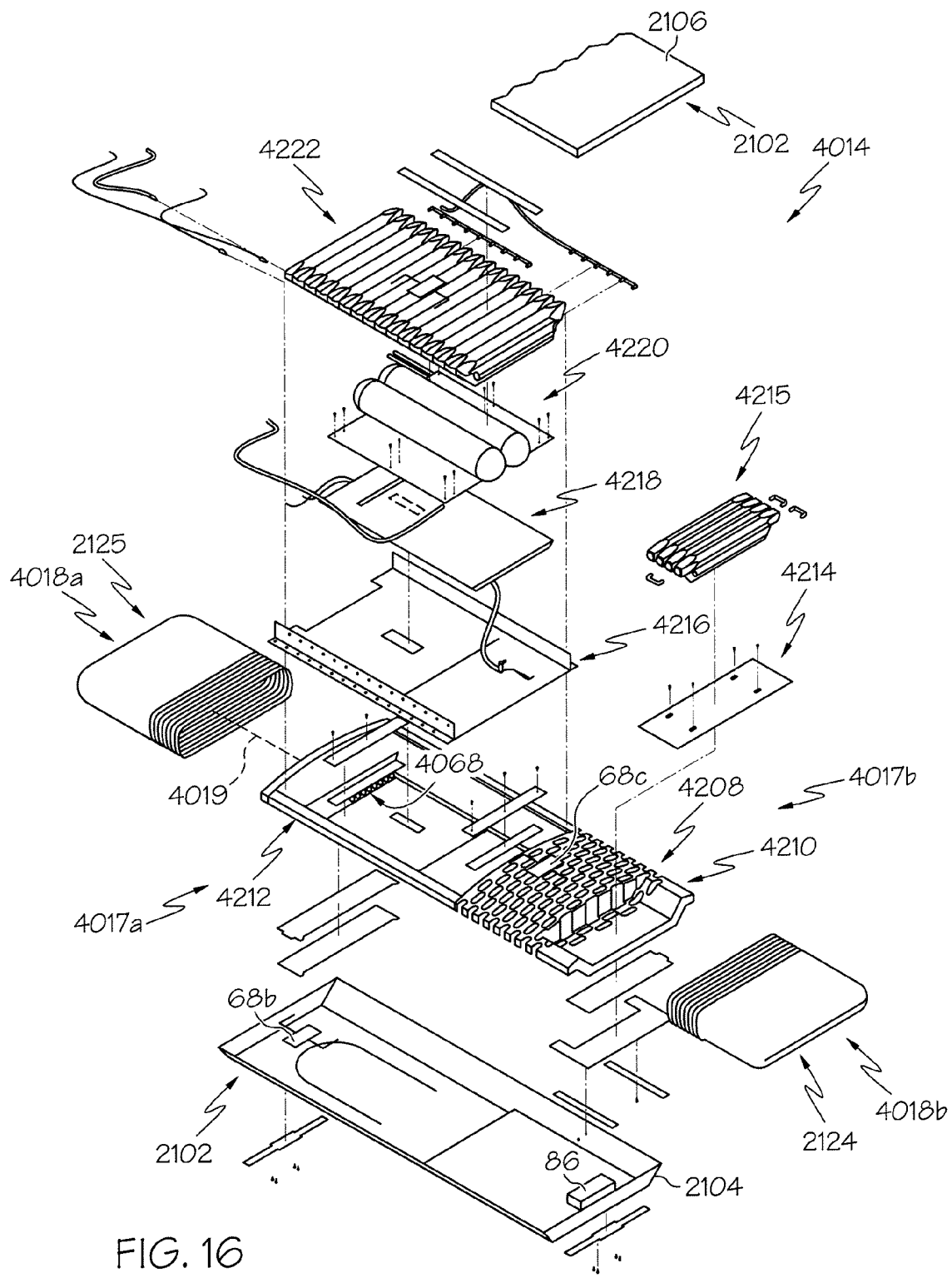
FIG. 16 is an exploded perspective view of an embodiment of a person support apparatus according to principles of the present disclosure.

FIG. 16 depicts an illustrative embodiment of a person support apparatus in the form of a modular mattress assembly 4014 to be supported by a deck of a patient support apparatus, such as those described above. In this example, the mattress assembly 4014 includes first and second sides 4017*a* and 4017*b* extending substantially parallel to a longitudinal center axis 4019 between head and foot ends 4018*a* and 4018*b*. The modular mattress assembly 4014 includes an outer cover 2102 having a bottom cover portion 2104 and a top cover portion 2106 which are configured, when coupled together, to provide an interior region in which a plurality of internal components including a foam receiving base 4208 are encapsulated. The receiving base 4208 includes a foam foot section 4210 and a foam body section 4212 coupled to the foot section 4210. Component mounting substrates 4214, 4216 are coupled to the foot section 4210 and the body section 4212, respectively, of the base 4208. A foot or heel bladder assembly 4215 is coupled to the mounting substrate 4214. A foam filler or panel 4218 is supported above the mounting substrate 4216 and is received within the base 4208.

A turn assist bladder assembly 4220 is received above the foam filler 4218 and is coupled to the mounting substrate 4216. An upper bladder assembly 4222 is received above the turn assist bladder assembly 4220 and is likewise coupled to the mounting substrate 4216. A fire sock or barrier 2124 is configured to surround the receiving base 4208, including the foot section 4210 and the body section 4212, the mounting substrates 4214 and 4216, the heel bladder assembly 4215, the foam filler 4218, the turn assist bladder assembly 4220, and the upper bladder assembly 4222. A shear cover 2125 is configured to be received over the fire barrier 2124. The top cover portion 2106 is configured to be coupled to the bottom cover portion 2104 to receive the other mattress components and to define the outer cover 2102. A mattress fluid connector 4068 is coupled to the bottom cover portion 2104 and is configured to provide fluid communication between a manifold (not shown), which is coupled to a pump (not shown), and the mattress 4014. The turn assist bladder 4220 is a moving component that can be utilized to assist the caregiver in turning the patient. In addition or as an alternative, the turn assist bladder 4220 can be utilized for providing continuous lateral rotation therapy to the patient, such as of the type known in the art for example. Such a therapy involves periodically rotating the patient from side to side, to reduce the risk of pressure sores. The upper bladder layer 4222 may be utilized to provide support and cushioning to the patient, and to provide alternating pressure therapy to the patient, such as known in the art for example. Thus, each upper bladder can be a moving component as well. Additional details of mattress assembly 4014 and the components for controlling the inflation thereof can be found in U.S. Pat. No. 7,296,312 which is hereby incorporated by reference herein.

In the illustrative embodiment of FIG. 16, sensors 68*a*, 68*b*, and 68*c* are fixed at various locations within the mattress to detect physiological signs of the patient. In this example, sensor 68*a* is located on top of the air bladder layer 4222 in order to provide a signal from the patient's mid section. Sensor 68*b* is located near the head end of the assembly, beneath the foam base layer 4208 and above the lower outer cover 2102. Accordingly, this sensor 68*b* can be used to provide a signal from the patient's upper body. Additionally, sensor 68*c* is located above the foam base 4208 and beneath the upper outer cover 2106. This sensor 68*c* can be utilized to provide a signal from the patient's seat area or lower body. The signals from these sensors are provided through wires in the mattress to a processor assembly 86, which in this example is provided within the mattress 4014. The processor of assembly 86 can then utilize the signals in any of the ways described herein, for alarming and detection of episode onset. The assembly 86 can be provided in an opening or recess on the bottom side of the foot foam section 4210. The cover 2102 can be in the form of a ticking that includes urethane, nylon, and/or an antimicrobial component such as silver for example.

Figure 17:
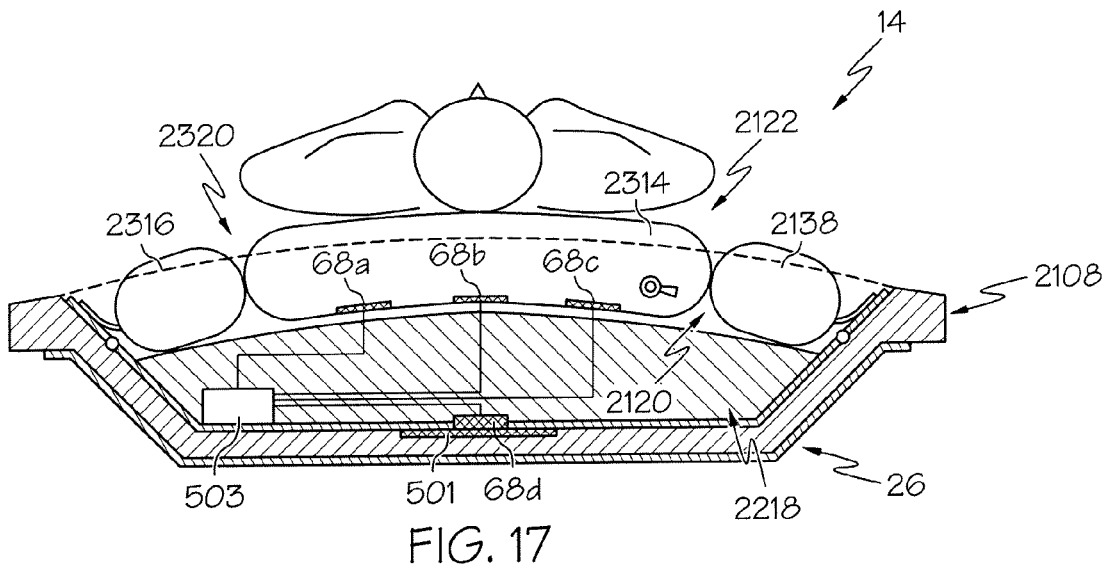
FIGS. 17-18 are cross-sectional views of an embodiment of a person support apparatus according to principles of the present disclosure, showing a feature of a mattress being applied via the movable component in the form of a turn bladder.
Figure 18:
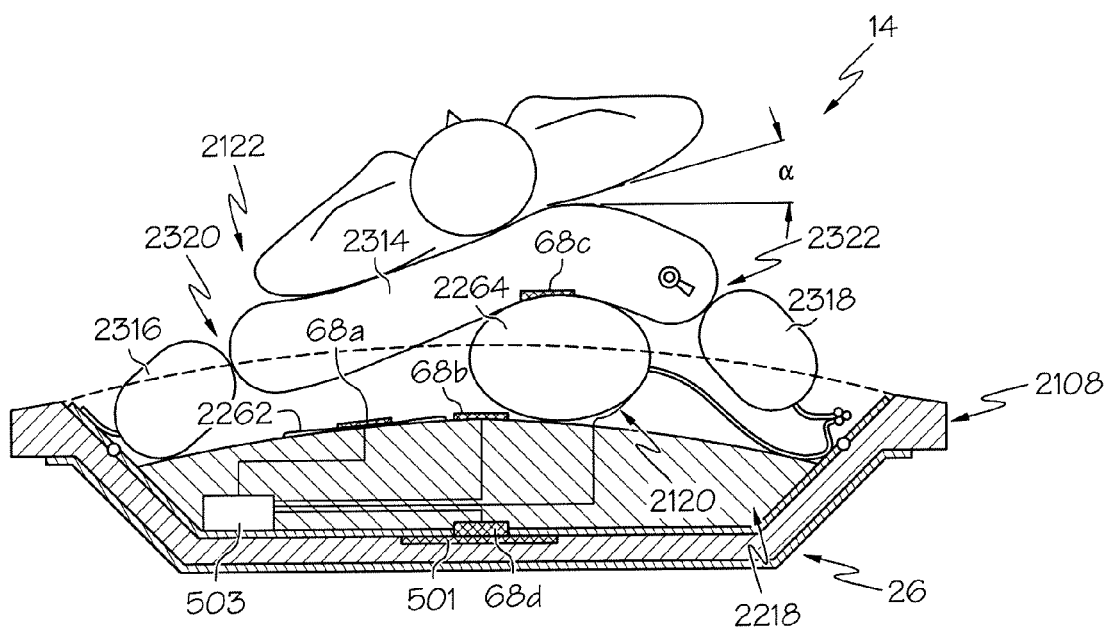

FIGS. 17 and 18 illustrate an embodiment of a mattress 14 including upper bladder assembly 2122 and turn assist bladder assembly 2120. More particularly, FIG. 17 illustrates a normal mode of operation with the head zone of the upper bladder assembly 2122 inflated, and the turn assist bladders 2262 and 2264 deflated. FIG. 18 illustrates a left turn assist mode of operation wherein the left turn assist bladder 2264 is inflated. Since the left turn assist bladder 2264 is laterally offset from the longitudinal center axis of the mattress 14, inflation of the bladder 2264 causes one side of the upper bladder assembly 2122 to raise above the other side. The hinges 2320 and 2322 between the side portions 2316 and 2318 and the center portion 2314 of the bladders 2306 of the upper bladder assembly 2122 permit the mattress 14 to substantially conform to the shape resulting from the inflation of the left turn assist bladder 2264. In an illustrative embodiment, upon inflation of one of the turn assist bladders 2262 and 2264, a patient supported on the mattress 14 is rotated by an angle α of approximately 20 degrees from horizontal. Upon completion of the turn assist, a control system 503 of mattress 14 causes the inflated turn assist bladder 2262, 2264 to vent to atmosphere. Simultaneously, the upper bladder assembly 2122 is instructed by the central system 503 to inflate to a maximum pressure.

Since the turn assist bladder assembly 2120 is sandwiched intermediate the upper bladder assembly 2122 and a crowning core 2218, inflation of the upper bladder assembly 2122 facilitates the rapid venting of air within the turn assist bladders 2262 and 2264 to atmosphere. In this embodiment, the foam crowning core 2218 is received within the channel defined by the sidewalls and the body section of the receiving base 2108. The core 2218 may be composed of a plurality of substantially planar layers of foam which are affixed together using conventional means, such as an adhesive.

In this embodiment, the mattress assembly 14 is fitted with several vital signs sensors. Here, three sensors 68*a*, 68*b*, and 68*c* are provided beneath the center portion 2314 of the upper bladder assembly/layer 2122 and above the foam layer portion 2218. Additionally, a fourth sensor 68*d* is provided beneath the center of the foam layer 2218 but inside the cover layer 26. Accordingly, the patient's vital signs can be detected from multiple locations inside the mattress assembly 14, by placing the sensors within differing layers and allowing for multiple signals to be determined. In this example, the sensors 68a and 68c are placed between the bladder 2314 and the turning bladders 2262 and 2266, so that the vital sign detection need not occur through the large turning bladder. In other embodiments, the sensors 68a, 68b, and 68c can be placed on top of the center bladder 2314 and below the top cover/ticking.

As shown in the example of FIGS. 17-18, the sensors 68a, 68b, 68c, and 68d can electrically connect to the central processor system 503 located inside the mattress, such as within the foam portion 2218. This system 503 can include a processor and logic and other circuitry to receive the signals from the sensors and determine the patient's vital signs and/or determine the presence of an episode or determine the onset of an episode, such as has been described herein. The system 503 may also included wired or wireless communication circuitry to allow the physiological signal and/or alarm/episode to be transmitted to appropriate personnel and/or equipment. Such components can be located in a housing within a recess in the foam 2218.

As further shown in this embodiment, the sensor 68d is placed between the foam 2218 and the base 2108. The base 2108 can comprise a rigid material to allow for additional support of the sensor 68d if needed or desired. Metal, fiberglass, plastic, composites, and other rigid materials can be used for this purpose. An additional flat rigid support sheet or panel 501 can be placed under any of the sensors if needed or desired. Such a support 501 can likewise be made of a flat and relatively inflexible panel of fiberglass, plastic, composite, or other rigid material. An additional similar support sheet can be placed on top of the sensor if needed or desired.

In further embodiments, instead of a rigid material, the base 2108 can comprise a layer of foam. Accordingly, in such embodiments, the sensor 68d is held between two layers of foam 2108 and 2218. These layers 2108 and 2218 may comprise foams having differing durometers. For instance, each foam layer 2108 and 2218 may have a durometer in the range of between 7 and 78 lbs ILD, but the durometer of each layer is of a different value within this range.

Figure 19:
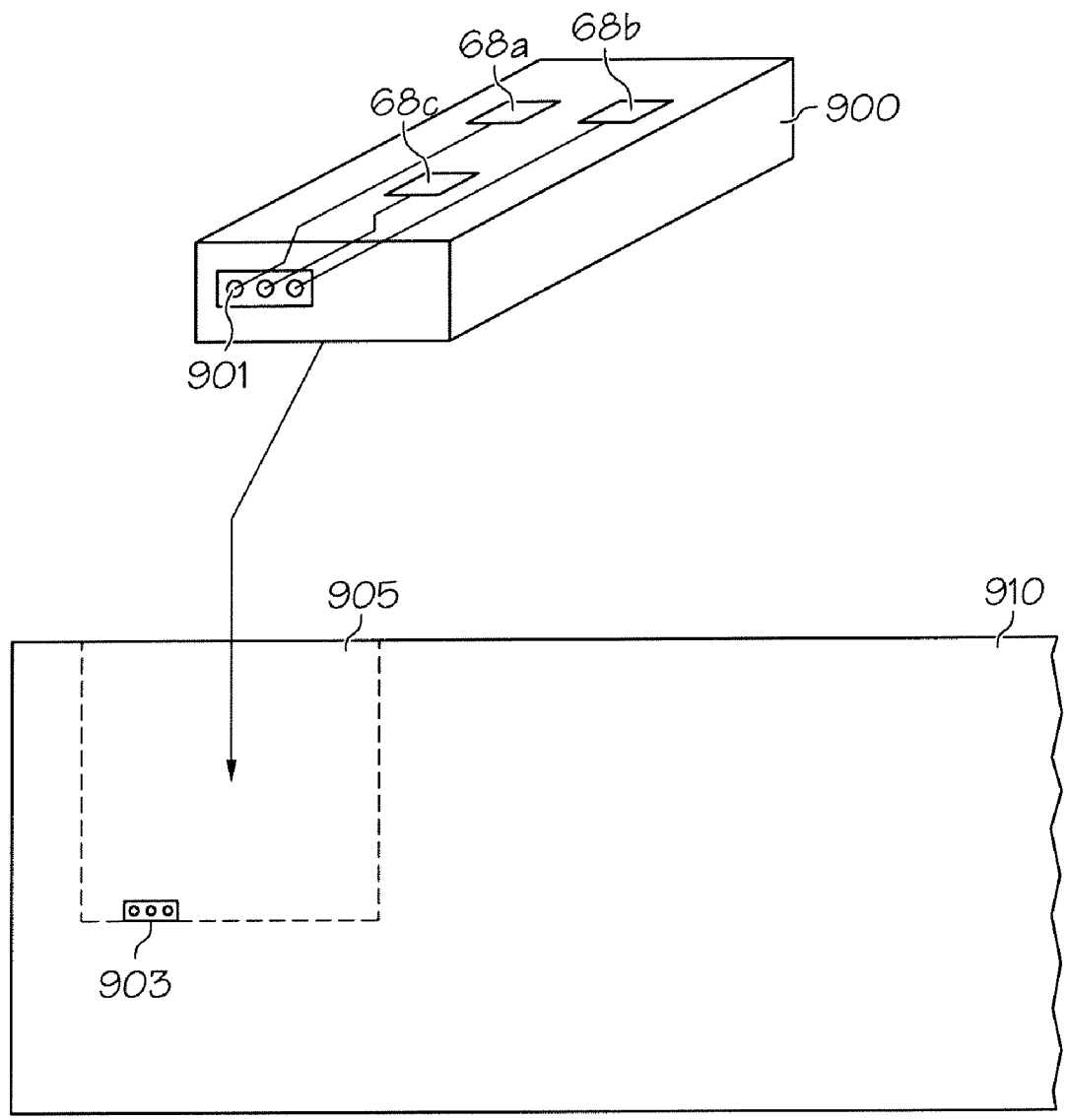
FIG. 19 is a schematic diagram of an embodiment of a sensor cassette module received within a patient support apparatus according to principles of the present disclosure.

FIG. 19 illustrates a further embodiment wherein the sensors 68a, 68b, and 68c are held within a cassette or module 901. The sensors 68a, 68b, and 68c connect to a connector 901 having male or female electrical connectors. The cassette 901 is sized and configured to fit within a corresponding recess 905 in a mattress assembly 910. The connector 901 of the cassette 900 is configured to connect with a corresponding connector 903 inside the recess 905. The connectors 901, 903 can snap together or fit via an interference fit, as can the cassette 900 and recess 905. The signals from the sensors 68a, 68b, and 68c can thus be sent through the connectors 901,903 and to the processor and other electronics in the mattress 910 or connected thereto. Accordingly, when it is desired to replace the sensors (e.g., due to wear or to upgrade), the cassette 901 can be disconnected by sliding the cassette 901 out of the recess 905, causing the connectors 901/903 to disconnect. A new cassette 901 with different sensors can then be placed into the recess 905.

The foregoing description of various embodiments and principles of the disclosure have been presented for the purposes of illustration and description. It is not intended to be exhaustive or to limit the disclosure to the precise forms disclosed. Many alternatives, modifications and variations will be apparent to those skilled in the art. Moreover, although multiple inventive aspects and principles have been presented, these need not be utilized in combination, and various combinations of inventive aspects and principles are possible in light of the various embodiments provided above. Accordingly, the above description is intended to embrace all possible alternatives, modifications, aspects, combinations, principles, and variations that have been discussed or suggested herein, as well as all others that fall within the principles, spirit and broad scope of the inventions defined by the claims.

The invention claimed is:

1. An apparatus for supporting and monitoring of a person, the apparatus comprising:
a bedframe,
a mattress support deck coupled to the bed frame, the mattress support deck including a head deck section that is made of substantially rigid material, that is movable between a raised position and a lowered position and that is sized and configured to support the person's upper body,
a sensing device fixed to the head deck section and configured to provide a monitoring signal indicative of at least one physiological sign of the person, the substantially rigid material of the head deck section being molded around the sensing device such that the sensing device is embedded in the head deck section, and
a processor coupled to the bedframe and configured to receive the monitoring signal.

2. The apparatus of claim 1, wherein the sensing device is embedded in the head deck section such that the sensing device is completely encased in the head deck section.

3. The apparatus of claim 1, wherein the head deck section is molded around the sensing device via at least one of injection molding, insert molding, fiberglass molding, pultrusion, and fiberglass layering processes.

4. The apparatus of claim 3, wherein the sensing device comprises a piezoelectric element that is placed under stress by stress that is induced in the head deck section during a molding process.

5. The apparatus of claim 1, wherein the sensing device comprises a housing and a piezoelectric diaphragm member within the housing.

6. The apparatus of claim 1, further comprising a second sensing device fixed to the bedframe and configured to sense at least one physiological sign of the person.

7. The apparatus of claim 1, wherein the mattress support deck comprises a seat deck section adjacent the head deck section and further comprising a second sensing device fixed to the seat deck section and configured to sense at least one physiological sign of the person.

8. The apparatus of claim 1, wherein the head deck section is substantially non-planar in shape.

9. The apparatus of claim 8, wherein the head deck section has a generally parabolic shape.

10. The apparatus of claim 8, wherein the head deck section is curved along its length and along its width.

11. The apparatus of claim 1, further comprising a waveguide coupled to the sensing device and configured to transmit energy to the sensing device.

12. The apparatus of claim 11, wherein the waveguide comprises at least one of the following: a beam member, a wire member, and a strip member.

13. The apparatus of claim 1, wherein the sensing device comprises an array of spaced apart piezoelectric sensor devices.

14. The apparatus of claim 1, wherein the head deck section has a first side edge and a second side edge and the sensing device is located about midway between the first and second side edges.

15. The apparatus of claim 1, wherein the sensing device is fixed to the head deck section at a central region of the head deck section.

* * * * *